US012788238B2

(12) United States Patent
Higashikawa et al.

(10) Patent No.: US 12,788,238 B2
(45) Date of Patent: Nov. 10, 2026

(54) CONTRAST-SENSITIVITY TEST DEVICE, OPTICAL-ELEMENT EVALUATION DEVICE, CONTRAST-SENSITIVITY TEST METHOD, AND OPTICAL-ELEMENT EVALUATION METHOD

(71) Applicants: NAC IMAGE TECHNOLOGY INC., Tokyo (JP); HOPNIC LABORATORY Co., Ltd., Fukui (JP)

(72) Inventors: Takuji Higashikawa, Yokohama (JP); Kuniyuki Matsuu, Yokohama (JP); Mikio Wada, Yokohama (JP); Teruyoshi Tomiyama, Echizen-cho (JP)

(73) Assignees: NAC IMAGE TECHNOLOGY INC., Tokyo (JP); HOPNIC LABORATORY CO., LTD., Fukui (JP)

( * ) Notice: Subject to any disclaimer, the term of this patent is extended or adjusted under 35 U.S.C. 154(b) by 376 days.

(21) Appl. No.: 18/569,498

(22) PCT Filed: Sep. 14, 2022

(86) PCT No.: PCT/JP2022/034482
§ 371 (c)(1),
(2) Date: Dec. 12, 2023

(87) PCT Pub. No.: WO2023/042869
PCT Pub. Date: Mar. 23, 2023

(65) Prior Publication Data

US 2024/0285162 A1 Aug. 29, 2024

(30) Foreign Application Priority Data

Sep. 14, 2021 (JP) ................................ 2021-149799

(51) Int. Cl.
*A61B 3/02* (2006.01)
*A61B 3/00* (2006.01)
(Continued)

(52) U.S. Cl.
CPC ............ *A61B 3/022* (2013.01); *A61B 3/0033* (2013.01); *A61B 3/005* (2013.01); *A61B 3/0091* (2013.01);
(Continued)

(58) Field of Classification Search
CPC ....... A61B 3/022; A61B 3/0033; A61B 3/005; A61B 3/0091; A61B 3/112; A61B 3/14;
(Continued)

(56) References Cited

U.S. PATENT DOCUMENTS 5,216,458 A * 6/1993 Andera .................... A61B 3/02
351/243
6,045,515 A * 4/2000 Lawton .................. A61B 3/022
351/239
(Continued)

FOREIGN PATENT DOCUMENTS

JP 2003-199712 A 7/2003
JP 2003-225205 A 8/2003
(Continued)

OTHER PUBLICATIONS

"CSV-1000/CSV-1000HGTi", Nikon Solutions Co., Ltd., 6 pgs, with English Translation.
(Continued)

*Primary Examiner* — Matthew Y Lee
(74) *Attorney, Agent, or Firm* — Greenblum & Bernstein, P.L.C.

(57) ABSTRACT

Provided is a contrast-sensitivity test device that is smaller than conventional ones and that enables a desired illumination environment to be easily set and enables a contrast sensitivity test to be conducted easily and accurately. The contrast-sensitivity test device includes: an illumination unit that emits illumination light such that a field of view of a subject is in a specified illumination environment; a visual
(Continued)

target presentation unit that is located within the field of view of the subject and that switches and sequentially presents a plurality of visual targets having different contrasts; a response-time measurement unit that, when the illumination light is emitted, measures a response time after each visual target is presented until the subject recognizes the visual target; and a casing that houses the illumination unit, the visual target presentation unit, and the response-time measurement unit.

20 Claims, 16 Drawing Sheets

(51) Int. Cl.

| | |
|---|---|
| ***A61B 3/11*** | (2006.01) |
| ***A61B 3/14*** | (2006.01) |
| ***G06T 7/00*** | (2017.01) |
| ***G06T 7/62*** | (2017.01) |
| ***G06T 7/70*** | (2017.01) |

(52) U.S. Cl.
CPC ................ *A61B 3/112* (2013.01); *A61B 3/14* (2013.01); *G06T 7/0012* (2013.01); *G06T 7/62* (2017.01); *G06T 7/70* (2017.01); *G06T 2207/10048* (2013.01); *G06T 2207/30041* (2013.01)

(58) Field of Classification Search
CPC ........... A61B 3/0008; A61B 3/06; A61B 3/10; A61B 3/11; A61B 3/113; A61B 5/16; A61B 3/032; A61B 3/066; A61B 3/024; A61B 3/0025; A61B 3/028; A61B 3/063; A61B 3/0041; A61B 3/02; A61B 3/00; G06T 7/0012; G06T 7/62; G06T 7/70; G06T 2207/10048; G06T 2207/30041; G06T 351/216; G06T 351/223; G06T 351/224; G06T 351/238; G06T 351/239; G06T 351/242; G06T 351/246; G16H 40/63; G16H 40/67; G16H 50/20; G02B 2027/0185; G02B 27/0172; G06F 3/013
See application file for complete search history.

(56) References Cited

U.S. PATENT DOCUMENTS

| | | | | |
|---|---|---|---|---|
| 6,361,167 | B1 * | 3/2002 | Su | A61B 3/107 351/206 |
| 2003/0164923 | A1 * | 9/2003 | Hirohara | A61B 3/06 351/216 |
| 2004/0095556 | A1 * | 5/2004 | Mihashi | A61B 3/112 351/238 |
| 2007/0236666 | A1 * | 10/2007 | Artigas Verde | A61B 3/024 351/224 |
| 2014/0211164 | A1 | 7/2014 | Nakamura | |
| 2017/0042418 | A1 * | 2/2017 | Leinonen | A61B 3/005 |
| 2017/0049316 | A1 * | 2/2017 | Donaldson | A61B 3/0033 |
| 2017/0273553 | A1 * | 9/2017 | Greivenkamp, Jr. | A61B 3/0041 |
| 2018/0296084 | A1 | 10/2018 | Kawahara et al. | |
| 2023/0255477 | A1 * | 8/2023 | Aibara | A61B 3/024 351/237 |

FOREIGN PATENT DOCUMENTS

| | | | | |
|---|---|---|---|---|
| JP | 2007-20919 | A | 2/2007 | |
| JP | 2009-240638 | A | 10/2009 | |
| JP | 2011-161122 | A | 8/2011 | |
| JP | 2014-87660 | A | 5/2014 | |
| JP | 2014-147427 | A | 8/2014 | |
| JP | 5778109 | B2 | 9/2015 | |
| WO | 02/062208 | A1 | 8/2002 | |
| WO | 2017/022757 | A1 | 2/2017 | |
| WO | WO-2021209669 | A1 * | 10/2021 | A61B 3/0008 |

OTHER PUBLICATIONS

"Megane Super Total Eye Premium Test", VH Retail Service Co., LTD., 8pgs, with English Translation.

"Mitsui Chemicals Verifies Effects of NeoContrast Wavelength-Controlling Lenses", Mitsui Chemicals, Inc., 2021, 7 pgs.

International Search Report issued in WIPO Patent Application No. PCT/JP2022/034482, dated Dec. 6, 2022, along with an English translation thereof.

Written Opinion issued in WIPO Patent Application No. PCT/JP2022/034482, dated Dec. 6, 2022.

Office Action issued in Corresponding JP Patent Application No. 2023-548495, dated Jul. 7, 2026, along with an English translation thereof.

* cited by examiner (b)

(a)

(c)

(a)

(b)

(a)

(b)

(c)

(a)

(b)

(a)

(b)

(a)

(b)

CONTRAST-SENSITIVITY TEST DEVICE, OPTICAL-ELEMENT EVALUATION DEVICE, CONTRAST-SENSITIVITY TEST METHOD, AND OPTICAL-ELEMENT EVALUATION METHOD

TECHNICAL FIELD

The present invention relates to a contrast-sensitivity test device for testing the contrast sensitivity of the subject's eyes and an optical-element evaluation device including the contrast-sensitivity test device, and also relates to a contrast-sensitivity test method and an optical-element evaluation method.

BACKGROUND ART

There are contrast sensitivity tests conducted as testing techniques for evaluating the quality of vision including the symptoms of cataract and glaucoma and, in addition, performance evaluation of eyeglasses and contact lenses and the like. The contrast sensitivity test is a test for measuring the limits of the perceivable contrast. In general, a contrast-sensitivity test device including a plurality of striped visual targets having different contrasts is used, and the contrast sensitivity test is conducted by requesting the subject to answer the striped visual target whose contrast (in other words, the difference between white and black in the striped visual target) the subject can perceive.

In addition, when light with a strong intensity (glare) enters eyes, it causes temporary blindness and changes the contrast sensitivity. Hence, contrast-sensitivity test devices capable of a contrast sensitivity test under a glare environment (glare test) are also in practical use (for example, Non-Patent Literature 1).

In addition, to evaluate the performance of eyeglasses or the like, creating different illumination environments such as outdoors, indoors, outdoors at night, and the like and conducting contrast sensitivity tests under each illumination environment are also proposed (for example, Non-Patent Literature 2).

In recent years, wavelength-controlling lenses have been in practical use as lenses for eyeglasses and sunglasses to improve contrast sensitivity (for example, NeoContrast (registered trademark)) (for example, Patent Literature 1).

Wavelength-controlling lenses are for improving contrast sensitivity and visibility by cutting light with a specific wavelength (for example, 585 nm). Improvement in contrast sensitivity and visibility increases visibility response speed. Hence wavelength-controlling lenses for various uses are available for sale, aiming to reduce drivers' fatigue and improve sports performance (for example, Non-Patent Literature 3).

CITATION LIST

Patent Literature

Patent Literature 1: Japanese Patent No. 5778109

Non-Patent Literature

Non-Patent Literature 1: "CSV-1000/CSV-1000HGTi", [online], Nikon Solutions Co., Ltd., [retrieved on Sep. 10, 2021], the Internet <URL: https://www.ophthalmic.nsl.nikon.com/products/csv_1000/>

Non-Patent Literature 2: "Megane Super Total Eye Premium Test", [online], VH Retail Service Co., LTD, [retrieved on Sep. 10, 2021], the Internet <URL: https://www.meganesuper.co.jp/glasses/totaleye/premium/>

Non-Patent Literature 3: "Mitsui Chemicals Verifies Effects of NeoContrast Wavelength-Controlling Lenses", [online], Mitsui Chemicals, Inc., [retrieved on Sep. 10, 2021], the Internet <URL: https://jp.mitsuichemicals.com/jp/release/2021/2021_0119.htm>

SUMMARY OF INVENTION

Technical Problem

In general, the wavelength-controlling lenses described in Non-Patent Literature 3 are sold in eyeglass shops, sports shops, or the like. However, the contrast-sensitivity test device described in Non-Patent Literature 1 is susceptible to the illumination of a test room, and thus it is difficult to conduct a contrast sensitivity test accurately. For the contrast-sensitivity test device described in Non-Patent Literature 2, the illumination environment of the entire test room needs to be controlled, which increases the size of the system. Hence, in reality, contrast sensitivity tests are not conducted in common shops (in other words, it is impossible to experience (evaluate) the effects of wearing wavelength-controlling lenses).

In addition, because the contrast sensitivity test described in Non-Patent Literature 1 and Non-Patent Literature 2 is a test in which the subject is requested to answer striped visual targets whose contrast the subject can perceive (in other words, a subjective test), the accuracy in obtained test results is also an issue to be improved.

The present invention has been made in light of the situation described above, and an object thereof is to provide a contrast-sensitivity test device that is smaller than conventional ones and that enables a desired illumination environment to be easily set and enables contrast sensitivity to be tested easily and accurately. In addition, it is also an object to provide an optical-element evaluation device that includes the contrast-sensitivity test device mentioned above and enables optical elements such as lenses for eyeglasses and sunglasses to be easily evaluated. Further, it is also an object to provide a contrast-sensitivity test method that enables contrast sensitivity to be tested easily and accurately and to provide an optical-element evaluation method that enables optical elements to be easily evaluated by using the contrast-sensitivity test method mentioned above.

Solution to Problem

To achieve an object mentioned above, a contrast-sensitivity test device of the present invention includes: an illumination unit that emits illumination light such that a field of view of a subject is in a specified illumination environment; a visual target presentation unit that is located within the field of view of the subject and that switches and sequentially presents a plurality of visual targets having different contrasts; a response-time measurement unit that, when the illumination light is emitted, measures a response time after each visual target is presented until the subject recognizes the visual target; and a casing that houses the illumination unit, the visual target presentation unit, and the response-time measurement unit.

It is desirable that the visual target presentation unit present a reference visual target approximately at a center portion of the field of view of the subject and present each visual target at a position different from the position of the reference visual target for a specified time.

In this case, it is desirable that the positions at which the plurality of visual targets are presented be different from one another.

In this case, it is desirable that the response-time measurement unit detect a first line of sight when the subject visually recognizes the reference visual target and a second line of sight when the subject visually recognizes each visual target, determine a line-of-sight vector from the first line of sight and the second line of sight, and measure the response time from the line-of-sight vector.

In this case, it is desirable that the response-time measurement unit include three or more IR illumination devices each of which emits testing light toward an eyeball of the subject, an image capturing device that captures a reflected image formed by the testing light reflected on the eyeball, and a line-of-sight vector calculation unit that calculates the line-of-sight vector from the reflected image.

It is also desirable that the response-time measurement unit include an input unit that receives an input from the subject, and the response-time measurement unit measure the time after each visual target is presented until the input unit receives an input, as the response time.

It is also desirable that the illumination unit emit the illumination light toward an eyeball of the subject such that the subject feels dazzled.

It is also desirable that the illumination unit be configured such that the color temperature of the illumination light is changeable.

It is also desirable that the illumination unit include a plurality of LED elements that emit light similar to natural light, a diffusion plate that diffuses the light emitted from the plurality of LED elements, and a color-temperature conversion filter that converts the light having passed through the diffusion plate, into the illumination light having a specified color temperature, and the color-temperature conversion filter be replaceable.

It is also desirable that the image capturing device capture an image of an eyeball of the subject and the periphery of the eyeball, and the contrast-sensitivity test device further include an image processing unit that calculates at least one of the palpebral fissure width and the pupil diameter of the subject from data of the image captured by the image capturing device.

It is also desirable that the visual target presentation unit include an image display device that displays an image of each visual target.

It is also desirable that the visual target presentation unit include a screen and a projection device that projects and displays each visual target on the screen.

It is also desirable that the visual target presentation unit include a plurality of screens on each of which a different one of the visual targets is displayed, and the screens be switched and sequentially placed within the field of view of the subject.

It is also desirable that each visual target have an approximately circular shape in which brightness varies according to a two-dimensional Gaussian function.

It is also desirable that the visual targets include a striped pattern in which a white line and a black line are repeated alternately.

In another aspect, an optical-element evaluation device of the present invention includes: any one of the contrast-sensitivity test devices described above; and an optical element that is placed in front of the eyeball of the subject so as to be replaceable.

In another aspect, a contrast-sensitivity test method of the present invention includes the steps of: emitting illumination light such that a field of view of a subject is in a specified illumination environment; switching and sequentially presenting a plurality of visual targets having different contrasts in the field of view of the subject; and measuring, when the illumination light is emitted, a response time after each visual target is presented until the subject recognizes the visual target.

In another aspect, an optical-element evaluation method of the present invention is an optical-element evaluation method that includes the steps of the contrast-sensitivity test method described above and further includes the step of placing an optical element in front of an eyeball of the subject.

Advantageous Effects of Invention

As described above, the present invention can achieve a contrast-sensitivity test device that is smaller than conventional ones and that enables a desired illumination environment to be easily set and enables contrast sensitivity to be tested easily and accurately. In addition, it is also possible to achieve an optical-element evaluation device that includes the contrast-sensitivity test device mentioned above and enables optical elements to be easily evaluated. Further, it is also possible to achieve a contrast-sensitivity test method that enables contrast sensitivity to be tested easily and accurately and to achieve an optical-element evaluation method that enables optical elements to be easily evaluated by using the contrast-sensitivity test method mentioned above.

DESCRIPTION OF EMBODIMENTS

Hereinafter, embodiments of the present invention will be described in detail with reference to the drawings. Note that in the figures, the same or similar portions are denoted by the same symbols, and repetitive description thereof is omitted.

First Embodiment

[Configuration of Contrast-Sensitivity Test Device]

Figure 1:
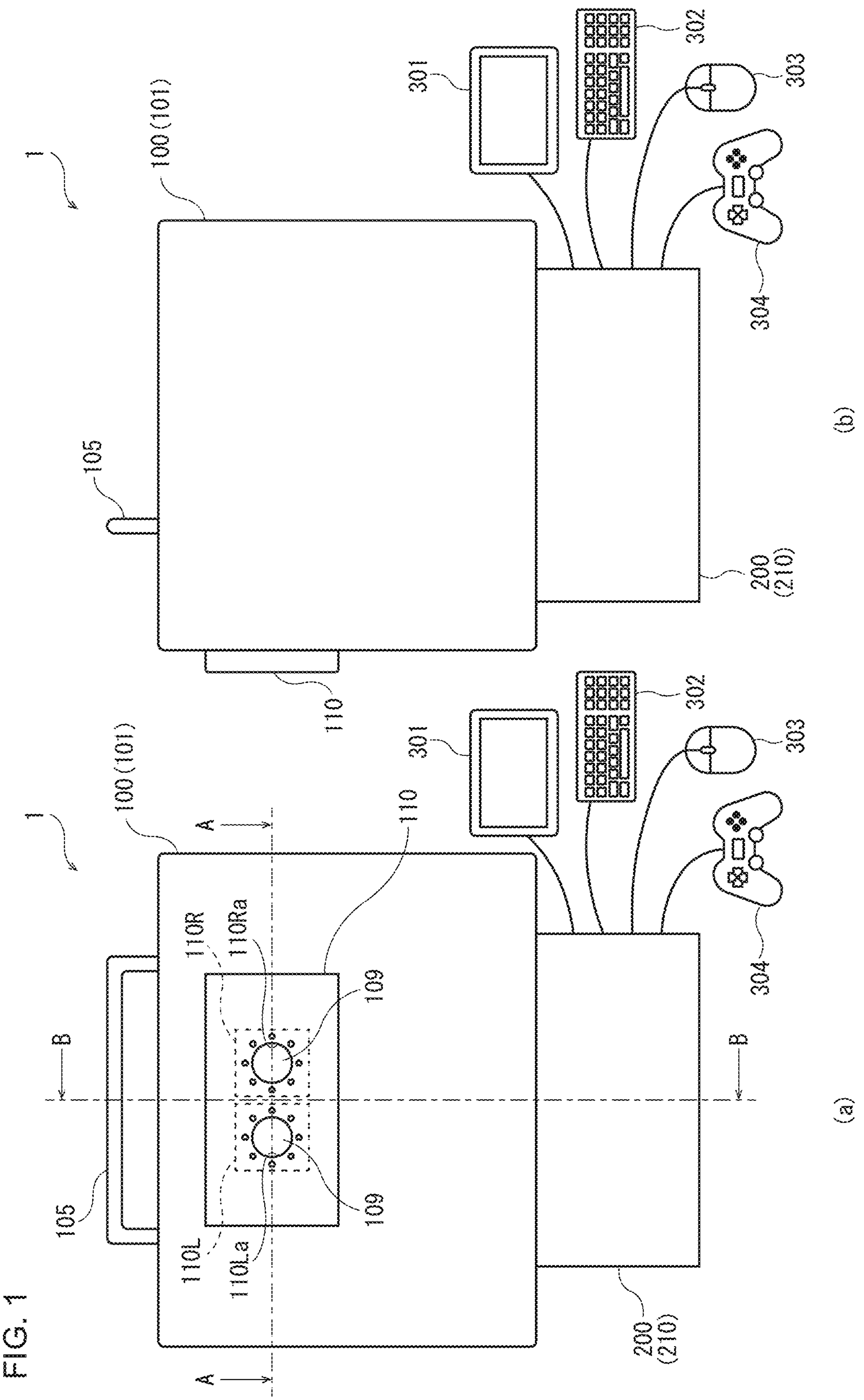
FIG. 1 shows diagrams illustrating the configuration of a contrast-sensitivity test device according to a first embodiment of the present invention.

FIG. 1 shows diagrams illustrating the configuration of a contrast-sensitivity test device 1 according to a first embodiment of the present invention. As illustrated in FIG. 1, the contrast-sensitivity test device 1 of the present embodiment is a device for testing the contrast sensitivity of the subject's eyes and includes a test unit 100 for testing the subject's eyes, a control unit 200 that controls the operation of the test unit 100, an external display 301, a keyboard 302, a mouse 303, and a controller 304. Note that FIG. 1(*a*) illustrates front views of the test unit 100 and the control unit 200, and FIG. 1(*b*) illustrates side views of the test unit 100 and the control unit 200.

The test unit 100 and the control unit 200 are formed integrally and configured to be placed on an inspection table (not illustrated) with adjustable height. In addition, a chin rest (not illustrated) with adjustable height for placing the subject's chin and a forehead support (not illustrated) are located between the subject and the test unit 100, so that the positions of the subject's eyes can be adjusted at the optimum positions for the test unit 100.

Figure 2:
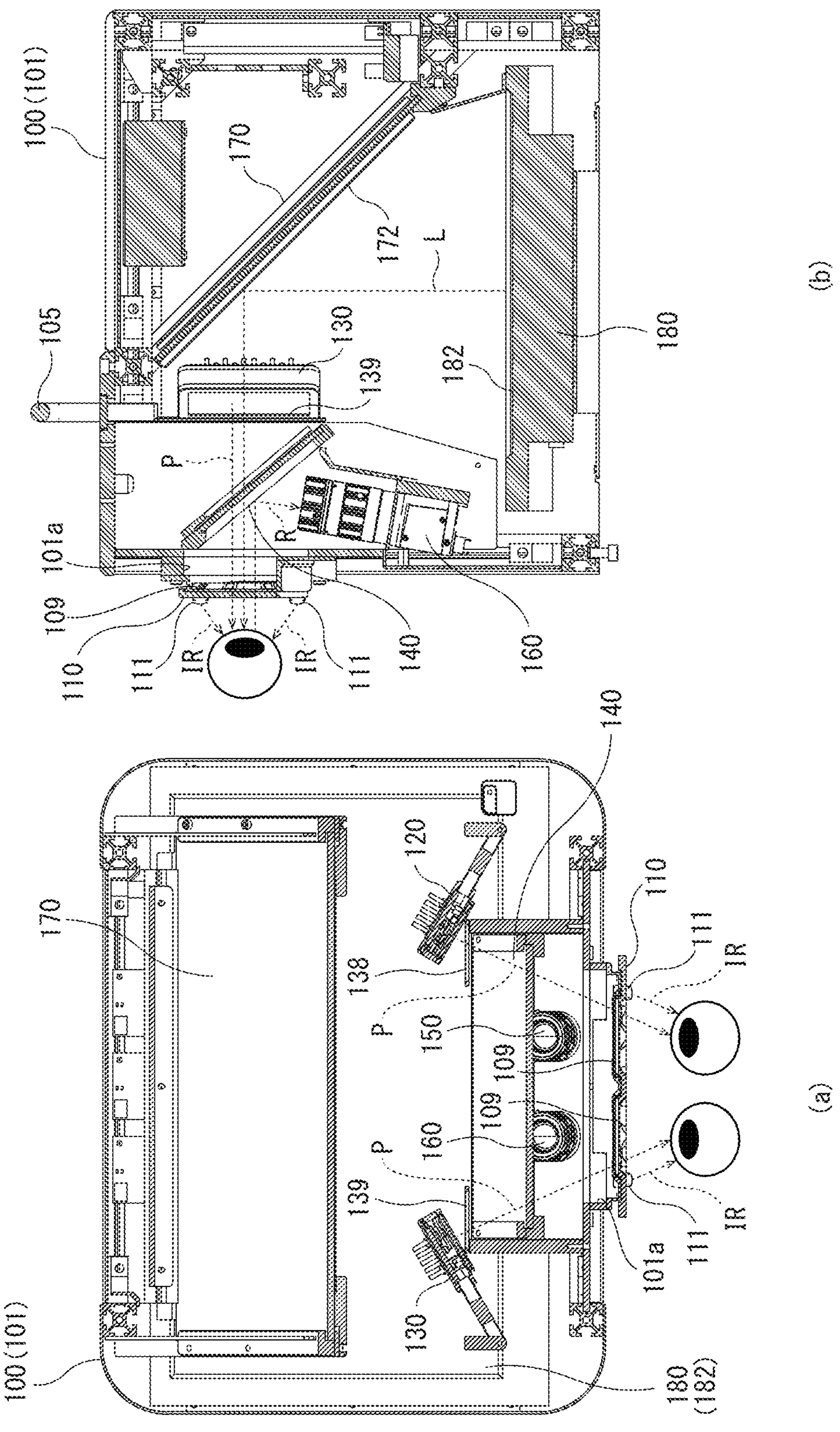
FIG. 2 shows cross-sectional view diagrams illustrating the configuration of a test unit of the contrast-sensitivity test device according to the first embodiment of the present invention.
Figure 3:
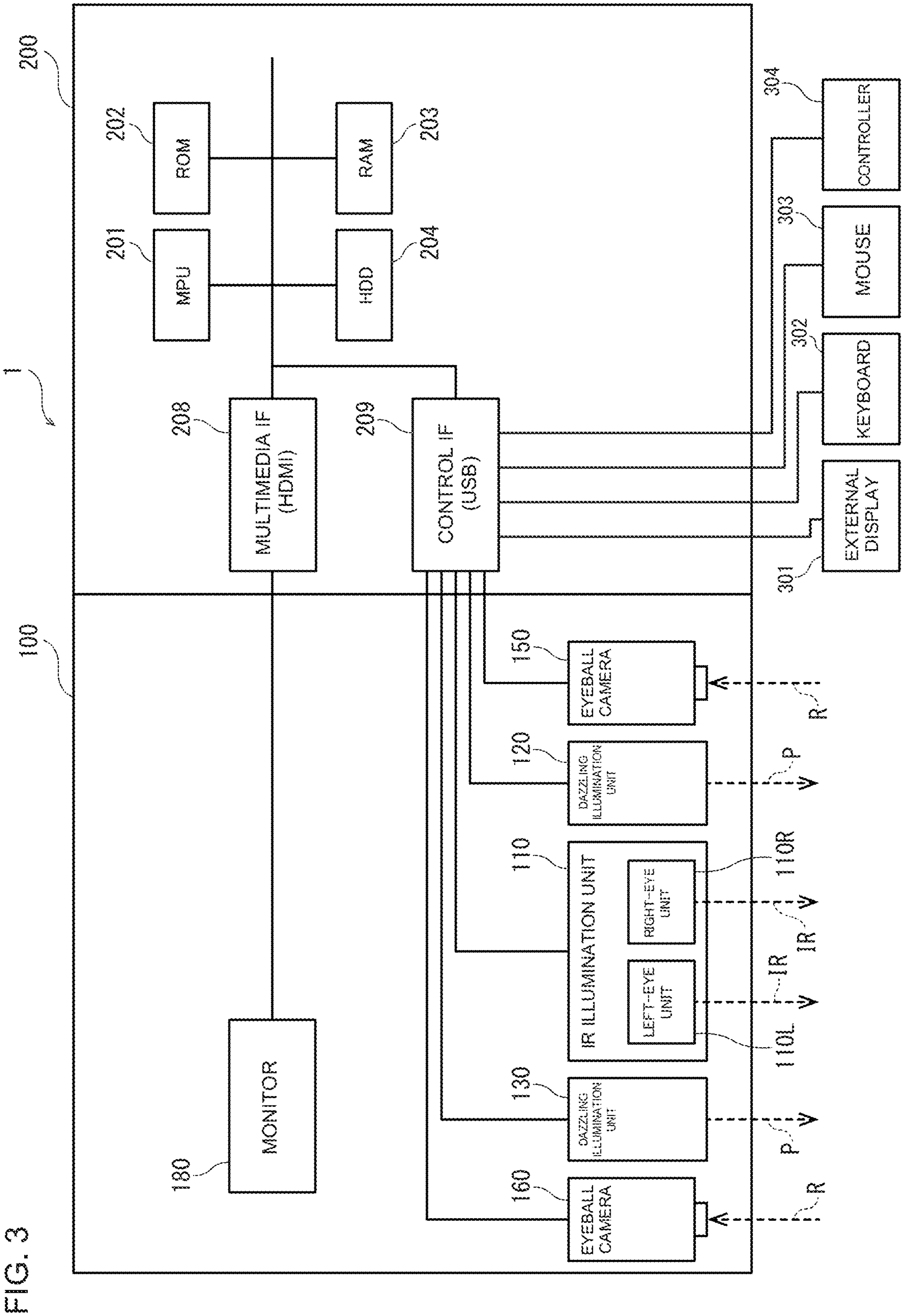
FIG. 3 is a block diagram for explaining electrical connections in the contrast-sensitivity test device according to the first embodiment of the present invention.

FIG. 2 shows cross-sectional view diagrams illustrating the configuration of the test unit 100 of the present embodiment. FIG. 2(*a*) is a cross-sectional view taken along line A-A in FIG. 1, and FIG. 2(*b*) is a cross-sectional view taken along line B-B in FIG. 1. FIG. 3 is a block diagram for explaining electrical connections in the contrast-sensitivity test device 1 of the present embodiment.

As illustrated in FIGS. 2 and 3, the test unit 100 of the present embodiment includes an upper casing 101, an IR illumination unit 110, dazzling illumination units 120 and 130, a hot mirror 140, eyeball cameras 150 and 160, a reflection mirror 170, and a monitor 180. The IR illumination unit 110, the dazzling illumination units 120 and 130, the eyeball cameras 150 and 160 are connected to the control unit 200 through internal wiring.

As illustrated in FIG. 3, the control unit 200 includes an MPU 201 which centrally controls the overall operation of the contrast-sensitivity test device 1, ROM 202 which is a nonvolatile storage for control data including the operating system (OS), RAM 203 which is a temporary storage for various kinds of data and is also used as a working area for the MPU 201, a storage device 204 (for example, a hard disk drive (HDD) or a solid state drive (SSD)) which stores various kinds of data and software in a nonvolatile and updatable manner, a multimedia interface (IF) 208 such as an HDMI (registered trademark) which performs interface operation for sound data and video (image) data, a control interface (IF) 209 which performs various control interface operations, and a lower casing 210 (FIG. 1) which houses these components.

The external display 301 is a display device that presents the operator various kinds of information. The keyboard 302 is an input device for the operator to input various kinds of data. The mouse 303 is a pointing device for the operator to perform various settings and operations. The controller 304 is a device for the subject to performs various inputs and operations (for example, direction input by lever operations, direction input by button operations, and operations by voice input). Note that the connections of the external display 301, the keyboard 302, the mouse 303, and the controller 304 do not necessarily need to be wired and can be wireless (for example, by Bluetooth (registered trademark), Wi-Fi (registered trademark), or Miracast).

Returning to FIG. 2, the casing 101 is approximately cubic metal case and houses the dazzling illumination units 120 and 130, the hot mirror 140, the eyeball cameras 150 and 160, the reflection mirror 170, and the monitor 180. The front face (the face on the subject side) of the casing 101 has a circular opening 101*a* that enables the subject to view images on the internal monitor 180. The opening 101*a* is provided with the IR illumination unit 110 attached so as to cover the opening 101*a*.

The IR illumination unit 110 is a light source device for detecting optical axis vectors described later and has a right-eye unit 110R and a left-eye unit 110L (FIGS. 1 and 3). The right-eye unit 110R and the left-eye unit 110L each include eight LEDs 111 to 118 each of which emits infrared light IR (FIGS. 2 and 3) toward the subject's eyes. Note that the LEDs 111 to 118 of the present embodiment are on/off controlled according to control signals from the control unit 200.

A circular opening 110Ra or 110La is formed inside the circular row of the LEDs 111 to 118 of each of the right-eye unit 110R and the left-eye unit 110L (FIG. 1). A transparent cover glass 119 is provided inside each of the openings 110Ra and 110La (between the openings 110Ra and 110La and the casing 101) so as to cover the openings 110Ra and 110La. With this configuration, the subject can view images on the internal monitor 180 through the cover glasses 119 at the openings 110Ra and 110La.

Figure 4:
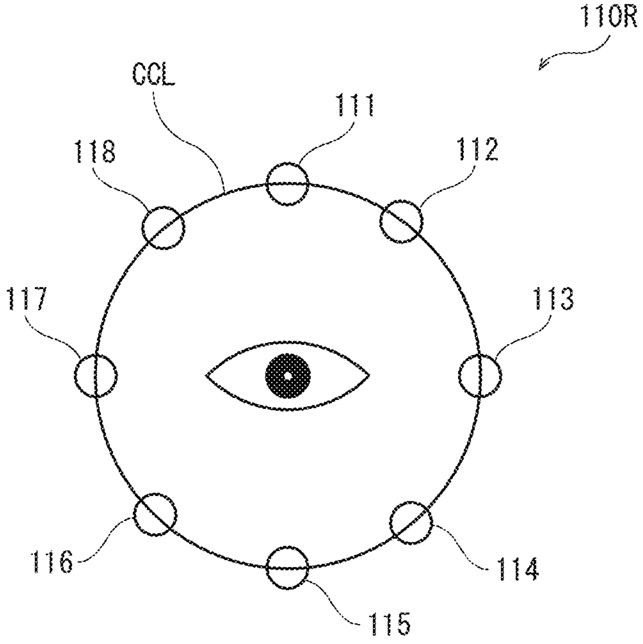
FIG. 4 is a diagram for explaining the arrangement of LEDs of an IR illumination unit of the contrast-sensitivity test device according to the first embodiment of the present invention.

FIG. 4 is a diagram for explaining the arrangement of the LEDs 111 to 118 of the right-eye unit 110R. As illustrated in FIG. 4, the LEDs 111 to 118 are arranged on the circumference of a circle CCL in a plane intersecting the visual axis of the subject (an axis intersecting the drawing plane) at equal angular intervals (every 45° (=360°/8) in the case of FIG. 4). Note that the arrangement of the LEDs 111 to 118 of the left-eye unit 110L is the same as or similar to the arrangement of the LEDs 111 to 118 of the right-eye unit 110R.

The dazzling illumination units 120 and 130 are light source devices for glare testing that emit illumination light P (FIGS. 2 and 3) toward the subject's eyeballs from the obliquely left front of the subject's left eye and the obliquely right front of the subject's right eye so that the subject feels dazzled (glare).

Figure 5:
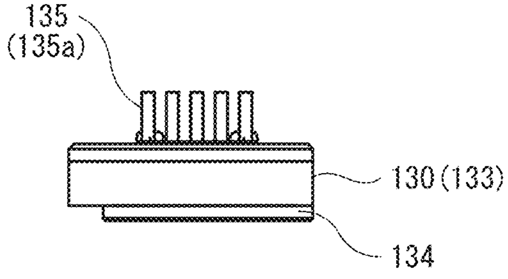
FIG. 5 shows diagrams for explaining the configuration of a dazzling illumination unit of the contrast-sensitivity test device according to the first embodiment of the present invention.
Figure 5:
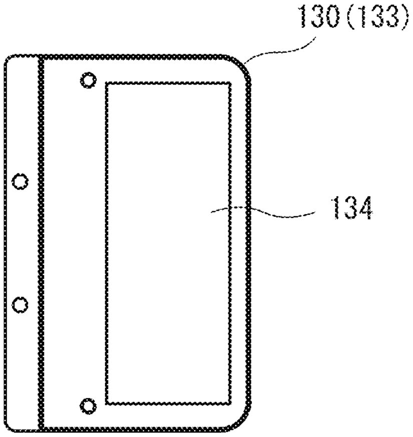
Figure 5:
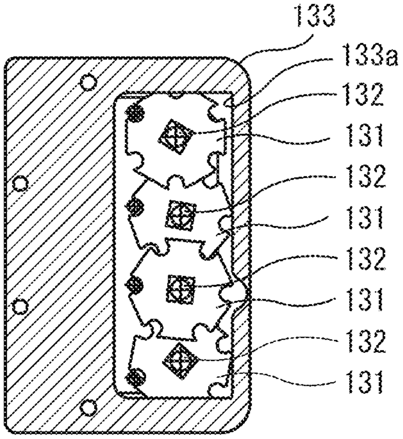

FIG. 5 shows diagrams for explaining the configuration of the dazzling illumination unit 130. FIG. 5(*a*) is its front view, FIG. 5(*b*) is its top view, and FIG. 5(*c*) is a cross-sectional view of an internal configuration. Note that the configuration of the dazzling illumination unit 120 is the same as that of the dazzling illumination unit 130, and hence, only the configuration of the dazzling illumination unit 130 will be described as a representative.

As illustrated in FIG. 5(*c*), the dazzling illumination unit 130 includes a plurality of (four in the example of FIG. 5(*c*)) substrates 131, an LED chip 132 placed on each substrate 131, a case 133 that houses the substrates 131 and the LED chips 132, a diffusion plate 134 located so as to cover an opening 133*a* in the front face of the case 133, and a heat sink 135 fixed to the back face of the case 133.

A surface of the substrate 131 has an anode pad (not illustrated) and a cathode pad (not illustrated) for supplying electric power to the LED chip 132, and each LED chip 132 is electrically connected to the anode pad and the cathode pad by soldering or the like. The anode pad and the cathode pad are electrically connected to a driver circuit (not illustrated), and each LED chip 132 is supplied with a specified drive current from the driver circuit according to a control signal from the control unit 200. When the drive current is supplied to each LED chip 132, each LED chip 132 emits light similar to natural light (including all of the wavelengths of visible light) (hereinafter simply referred to as "natural light") having an intensity according to the amount of the drive current. Note that in the present embodiment, on/off control (lighting time, lighting start timing, flashing, or the like) of the LED chips 132 and control of the light intensity (illuminance adjustment) of the LED chips 132 are performed according to control signals from the control unit 200.

The diffusion plate 134 is an optical member that diffuses natural light emitted from the LED chips 132. Since light from the LED chips 132 passes through the diffusion plate 134, natural light with less illumination unevenness (in other words, with approximately uniform illuminance) is emitted from the diffusion plate 134. Although the diffusion plate 134 of the present embodiment is fixed so as to cover the opening 133*a* in the front face of the case 133, the diffusion plate 134 may be changeable (replaceable) depending on the condition of glare testing, as a possible configuration.

The heat sink 135 is a member for dissipating heat generated in the LED chips 132 and is made of a metal with high thermal conductivity such as copper. The heat sink 135 of the present embodiment is an air-cooled heat sink having a plurality of heat dissipation fins 135*a*, and heat generated in the LED chips 132 is transmitted to the heat dissipation fins 135*a* through the substrates 131 and the case 133 and is dissipated from the heat dissipation fins 135*a* to air.

Natural light emitted from the dazzling illumination units 120 and 130 passes through color-temperature adjustment filters 138 and 139 (FIG. 2) located near the dazzling illumination units 120 and 130, respectively.

The color-temperature adjustment filters 138 and 139 are optical members for setting a condition of glare testing (in other words, illumination environment) and are configured to convert natural light emitted from the dazzling illumination units 120 and 130 into illumination light P having a specified color temperature and emits the illumination light P. The color-temperature adjustment filters 138 and 139 of the present embodiment are attached to a filter replacement handle 105, and the color-temperature adjustment filters 138 and 139 can be inserted and pulled out by vertically moving the filter replacement handle 105. Thus, the color-temperature adjustment filters 138 and 139 can be replaced with ones with a specified color temperature. For example, in the case of using the color-temperature adjustment filters 138 and 139 with a color temperature of 5000 K, the LED illumination environment simulates indoors, in the case of using the color-temperature adjustment filters 138 and 139 with a color temperature of 6500 K, the LED illumination environment simulates outdoors, and in the case of using the color-temperature adjustment filters 138 and 139 with a color temperature of 2500 K, the illumination environment simulates outdoors in the evening.

Note that the illuminance of the illumination light P can be changed variously by changing the intensity of light of the LED chips 132 according to control signals from the control unit 200, and in the present embodiment, the maximum illuminance of the illumination light P is approximately 4000 Lx.

In addition, although the condition of glare testing (in other words, illumination environment) is set by replacing the color-temperature adjustment filters 138 and 139 in the present embodiment, for example, as a possible configuration, a plurality of LED chips 132 having different color temperatures may be used instead of the color-temperature adjustment filters 138 and 139 so that the LED chips 132 to be turned on can be switched according to a desired condition. As another possible configuration, a plurality of LED chips 132 provided with filters having different color temperatures may be used, and the LED chips 132 to be turned on may be switched according to a desired condition.

The illumination light P having passed through the color-temperature adjustment filters 138 and 139 and converted into light having a specified color temperature heads toward the hot mirror 140 (FIG. 2). Since the hot mirror 140 is an optical element that allows visible light to pass through and reflects infrared light, the illumination light P from the color-temperature adjustment filters 138 and 139 passes through the hot mirror 140 and is emitted toward the subject's eyeballs.

The eyeball cameras 150 and 160 are image capturing devices used to detect optical axis vectors described later and to measure the subject's palpebral fissure widths and pupil diameters, and the eyeball cameras 150 and 160 capture images of the subject's eyeballs through the hot mirror 140. More specifically, each of the eyeball cameras 150 and 160 contains an image capturing lens (not-illustrated), a visible-light cut filter, and an image capturing element (for example, CCD, CMOS, or the like). The reflected light (reflected image) R from the subject's eyeballs illuminated by the illumination light P and the infrared light IR is reflected on the hot mirror 140, enters the eyeball cameras 150 and 160, and is collected by image capturing lenses. After the visible light component (in other words, the component of the illumination light P) is attenuated by the visible-light cut filter, images are captured by the image capturing elements (FIG. 2(*b*) and FIG. 3). The images captured by the eyeball cameras 150 and 160 are transmitted to and processed by the control unit 200.

The monitor 180 is a display device for presenting the subject with various visual targets (images) for a contrast sensitivity test. The various visual targets (images) displayed on the display surface 182 of the monitor 180 are emitted as display light L from the display surface 182 and reflected on a reflection surface 172 (the surface facing the display surface 182) of the reflection mirror 170, pass through the hot mirror 140, and enter the subject's eyes (FIG. 2(*b*)). Note that present embodiment is configured such that when the subject's eyes are accurately positioned relative to the openings 110Ra and 110La of the IR illumination unit 110, the display surface 182 of the monitor 180 is positioned in the field of view of the subject, and the subject can view the various visual targets (images).

[Contrast Sensitivity Test Method]

Figure 6:
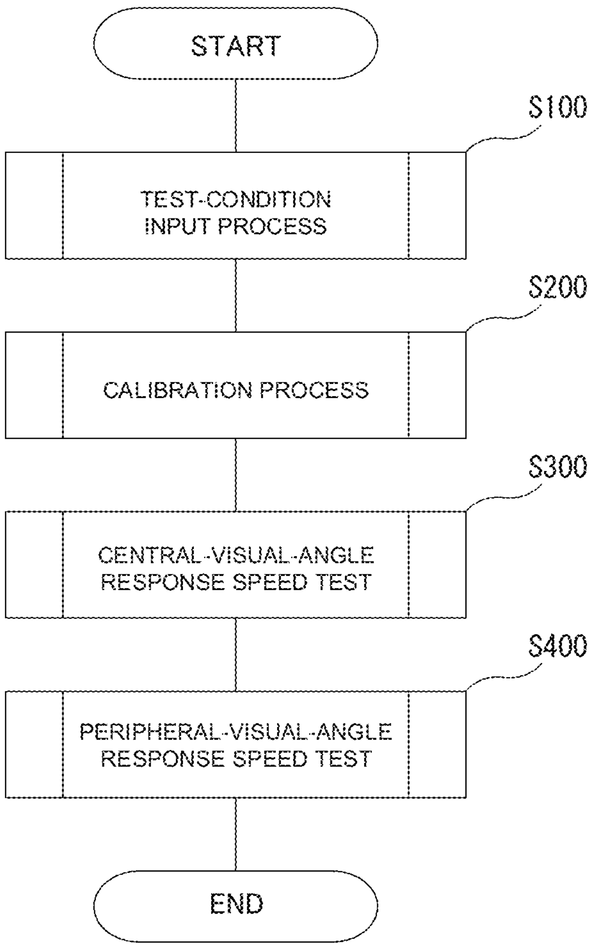
FIG. 6 is a flowchart for explaining a method of using the contrast-sensitivity test device according to the first embodiment of the present invention.

FIG. 6 is a flowchart for explaining a method of using the contrast-sensitivity test device 1 of the present embodiment (in other words, a test method). Specifically, FIG. 6 is a flowchart of operation when the operator operates the keyboard 302 and the mouse 303 to execute testing software stored in the hard disk 204.

As illustrated in FIG. 6, when the testing software is executed in the contrast-sensitivity test device 1, the processes (subroutines) of a test-condition input process $100, a calibration process S200, a central-visual-angle response speed test S300, and a peripheral-visual-angle response speed test S400 are executed.

[Test-Condition Input Process S100]

In the test-condition input process S100, the MPU 201 displays a specified input screen on the external display 301. The operator operates the keyboard 302 and the mouse 303 to fill out input items in the input screen, and after the input is finished, this process ends. Note that the input items include personal information on the subject such as his/her name, color temperature settings (illumination environment) and illuminance settings of the dazzling illumination units 120 and 130, settings of various parameters (the contrasts of striped visual targets DT1 to DT3 and the like) used in the central-visual-angle response speed test S300, and settings of various parameters (the number of visual targets CT, the contrasts of visual targets CT, presentation positions, and the like) used in the peripheral-visual-angle response speed test S400.

[Calibration Process S200]

Figure 7:
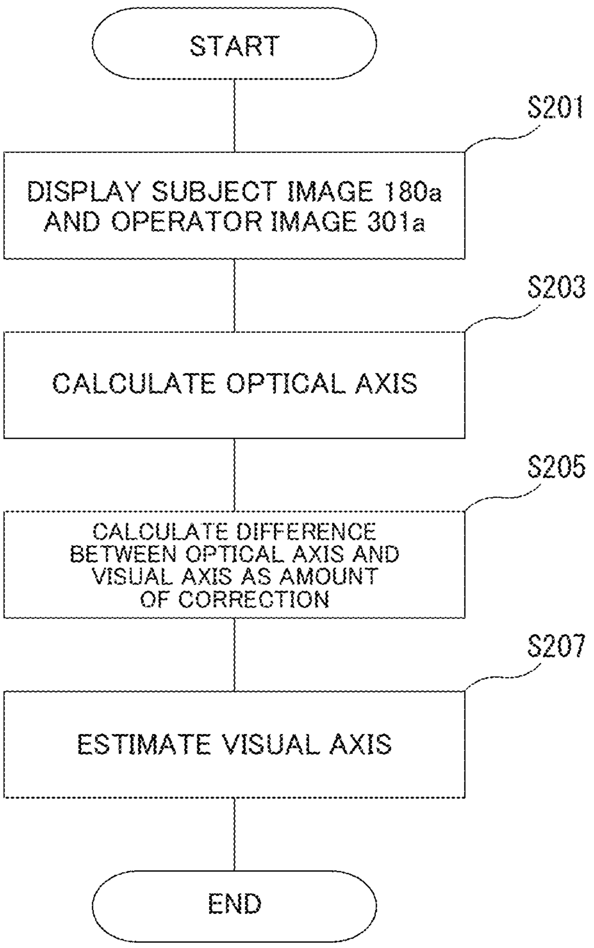
FIG. 7 is a flowchart of a calibration process executed by the contrast-sensitivity test device according to the first embodiment of the present invention.

The calibration process S200 is a process to correct individual differences in the sizes and shapes of the subject's eyes. FIG. 7 is a flowchart of the calibration process S200 executed by the MPU 201. The calibration process S200 of the present embodiment uses the optical-axis-vector calculation technique in a preceding patent application (Japanese Patent Application No. 2018-165668) filed by the inventors of the present invention and is a process the same as or similar to the visual-axis calibration in this patent application.

Figure 8:
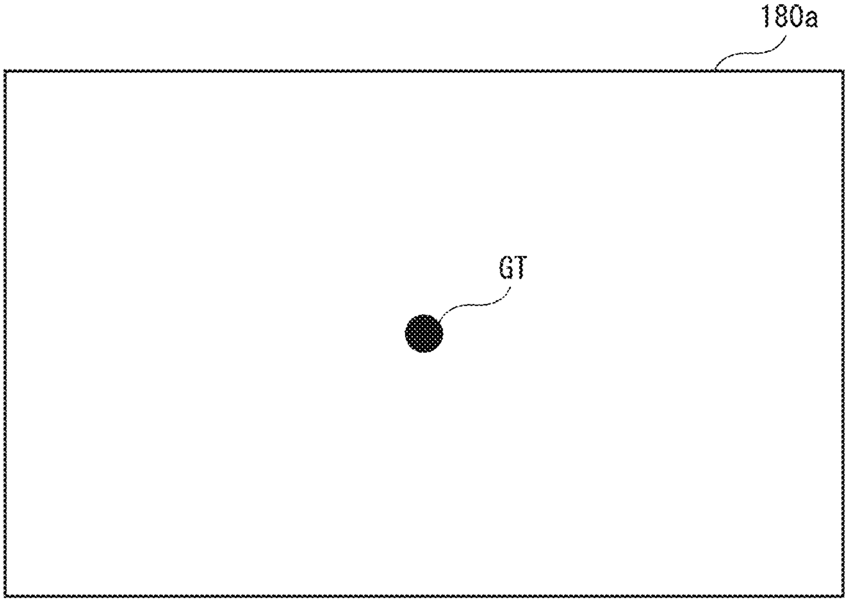
FIG. 8 shows a subject image and an operator image displayed in the calibration process in FIG. 7.
Figure 8:
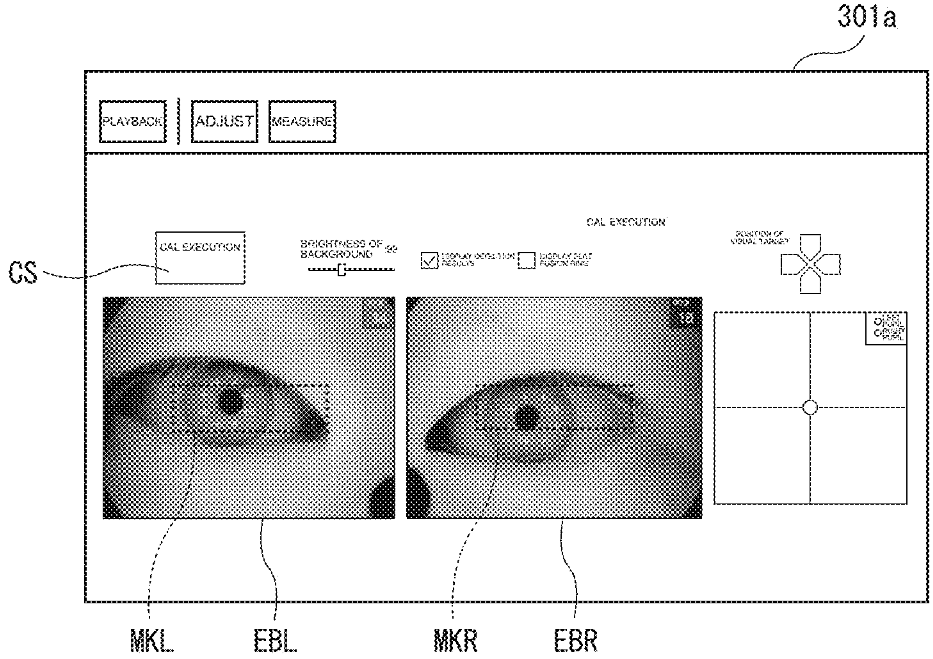

FIG. 8 shows diagrams of images displayed on the monitor 180 and the external display 301 in the calibration process S200. FIG. 8(*a*) is a subject image 180*a* displayed on the monitor 180 and provided to the subject, and FIG. 8(*b*) is an operator image 301*a* displayed on the external display 301 and provided to the operator.

When the calibration process S200 is executed, the MPU 201 displays the subject image 180*a* on the monitor 180, displays the operator image 301*a* on the external display 301, turns on the LEDs 111 to 118 of the IR illumination unit 110, and displays right and left eyeball images from the eyeball cameras 150 and 160 in eyeball-image display areas EBL and EBR in the operator image 301*a* (step S201). In this state, the subject is requested to look into the test unit 100 through the cover glasses 119 of the IR illumination unit 110, and the position of the subject's head is adjusted such that the subject's right and left pupils are within rectangular reference markers MKL and MKR.

Next, the subject is requested to gaze into a circular gaze visual target GT approximately at the center of the subject image 180*a*, and when the operator selects a CAL execution switch CS in the operator image 301*a* by operating the mouse 303, the process proceeds to step S203.

In step S203, the MPU 201 calculates the optical axes of both eyes.

More specifically, the MPU 201 calculates the average value of corneal curvature centers (a representative value of the corneal curvature center) of each of the subject's right and left eyeballs from the positions of the reflected images (bright spots around the pupil) of the LEDs 111 to 118 included in each of the right and left eyeball images form the eyeball cameras 150 and 160 and determines the center points of the right and left pupils from the right and left eyeball images. Then, the MPU 201 connects the corneal curvature center and the center point of the pupil and calculates the vector from the center point of the pupil to the corneal curvature center as the optical axis vector. Next, the process proceeds to step S205.

In step S205, the MPU 201 calculates the difference between the optical axis calculated in step S203 and the visual axis as the amount of correction.

More specifically, the MPU 201 calculates the difference between the position of the calculated optical axis and the position of the visual axis (line of sight) of the subject as the amount of correction such that the position of the calculated optical axis is in agreement with the visual axis (line of sight) of the subject gazing into the gaze visual target GT. Next, the process proceeds to step S207.

In step S207, the MPU 201 continuously calculates the optical axes (for example, at a period of 30 Hz) and corrects the calculated optical axes with the amount of correction calculated in step S205 to continuously estimates the visual axes of the subject (hereinafter referred to as "visual-axis detection process").

As described above, when the calibration process S200 is executed, the individual differences in the sizes and shapes of the subject's eyes are corrected, and the movement of the subject's visual axes (lines of sight) is continuously estimated accurately in the background.

After the calibration process S200 is finished, next, the central-visual-angle response speed test S300 is executed.

[Central-Visual-Angle Response Speed Test $300]

The central-visual-angle response speed test S300 is a contrast sensitivity test using visual targets the same as or similar to conventional striped visual targets.

Figure 9:
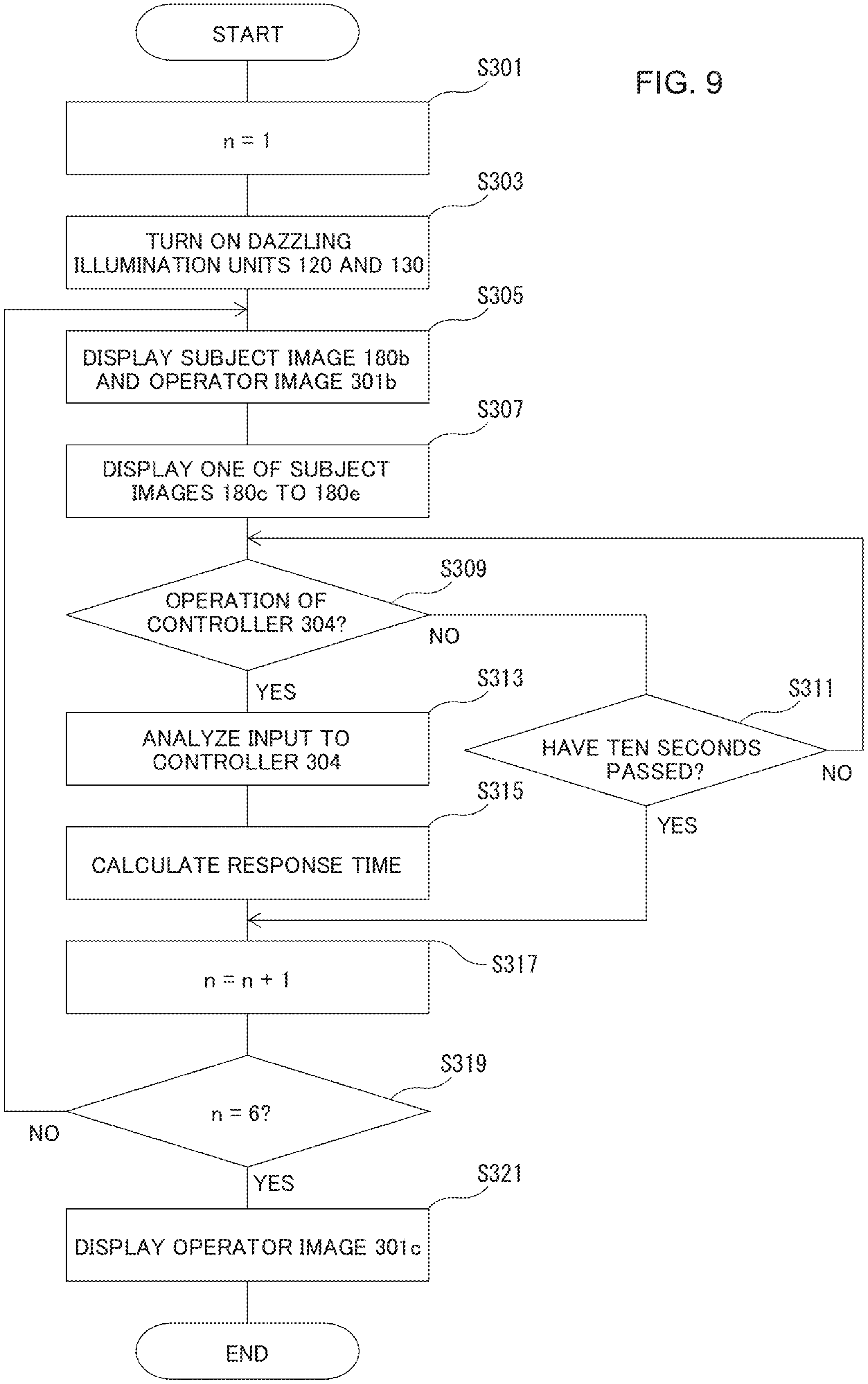
FIG. 9 is a flowchart of a central-visual-angle response speed test executed by the contrast-sensitivity test device according to the first embodiment of the present invention.
Figure 10:
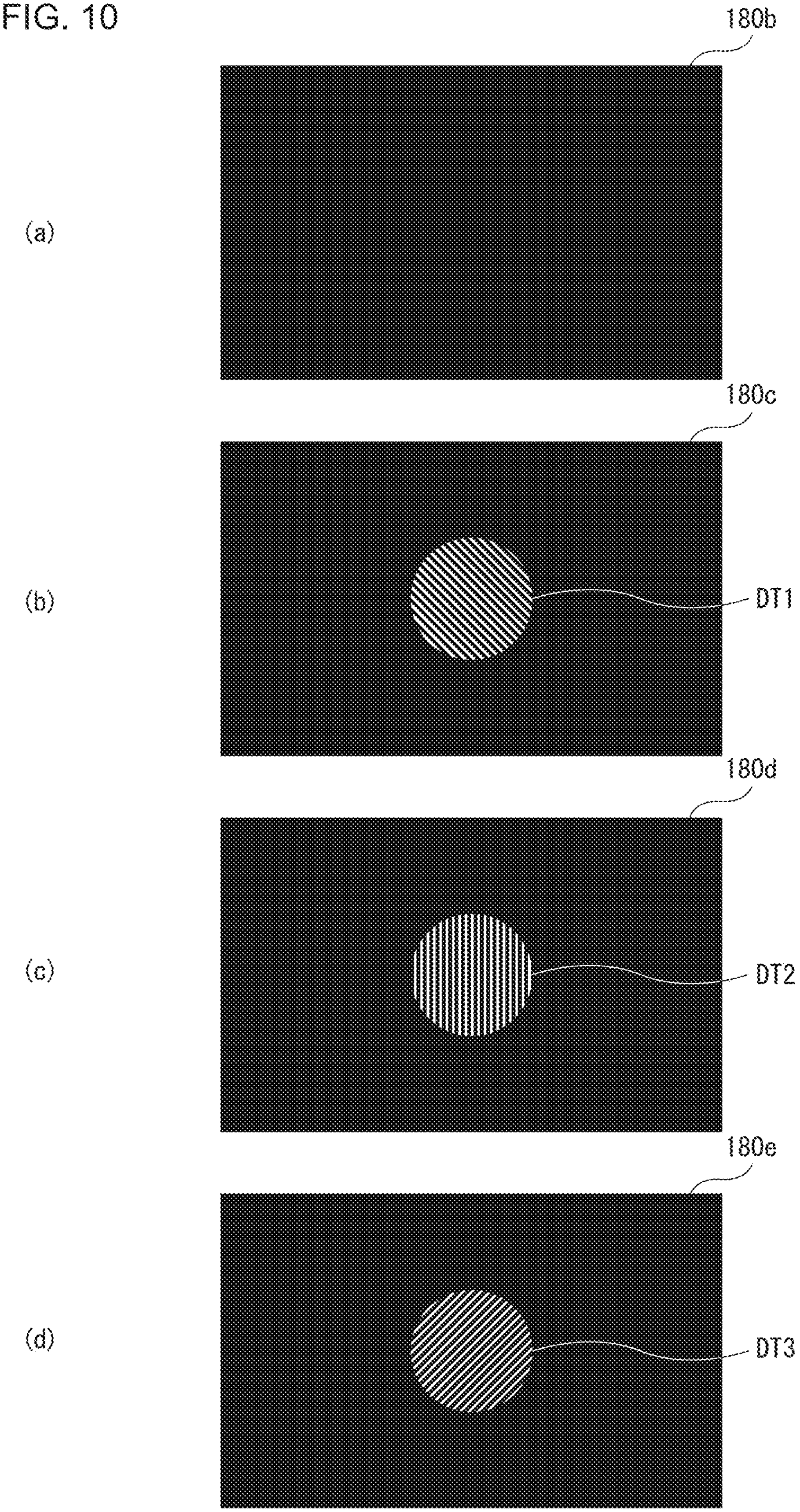
FIG. 10 shows subject images displayed in the central-visual-angle response speed test in FIG. 9.
Figure 11:
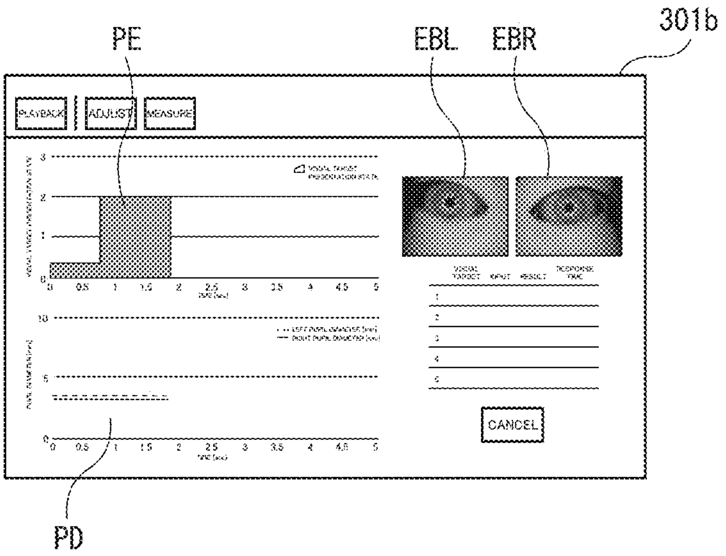
FIG. 11 shows operator images displayed in the central-visual-angle response speed test in FIG. 9.
Figure 11:
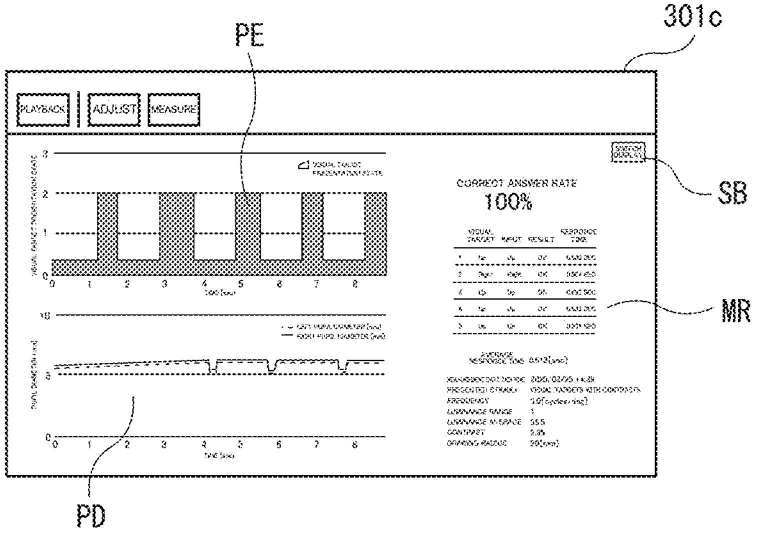
Figure 11:
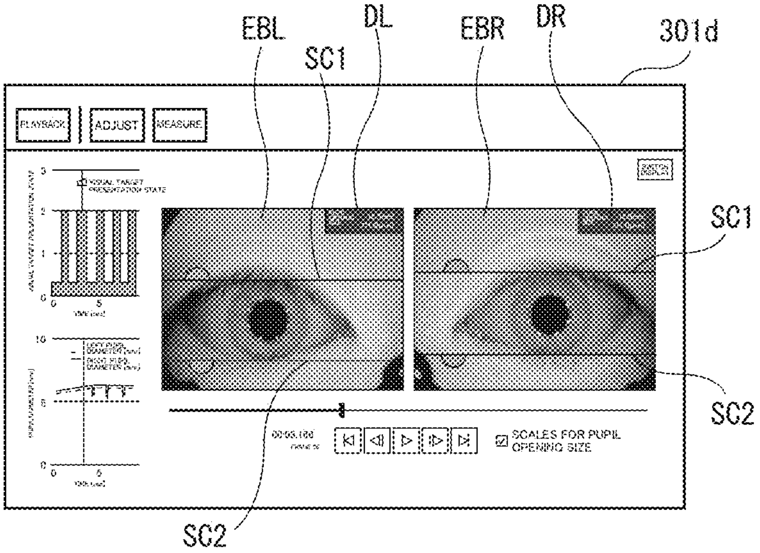

FIG. 9 is a flowchart of the central-visual-angle response speed test S300 executed by the MPU 201. FIG. 10 shows subject images 180*b* to 180*e* displayed on the monitor 180 and presented to the subject in the central-visual-angle response speed test S300. FIG. 11 shows operator images 301*b* to 301*d* displayed on the external display 301 and presented to the operator in the central-visual-angle response speed test S300.

When the central-visual-angle response speed test S300 is executed, the MPU 201 sets variable n for counting the number of tests to 1 (step S301) and turns on the dazzling illumination units 120 and 130 at a specified illuminance (in other words, turns on the LED chips 132 at a specified intensity) (step S303).

Next, the MPU 201 displays the subject image 180*b* (plain-color pattern) on the monitor 180 and displays the operator image 301*b* on the external display 301. The MPU 201 also turns on the LEDs 111 to 118 of the IR illumination unit 110 and displays the right and left eyeball images from the eyeball cameras 150 and 160 in the eyeball-image display areas EBL and EBR in the operator image 301*a* (step S305). Note that in the central-visual-angle response speed test S300 of the present embodiment, the diameters of the right and left pupils are continuously determined from the right and left eyeball images from the eyeball cameras 150 and 160. Next, the process proceeds to step S307.

In step S307, the MPU 201 presents one of the subject images 180*c* to 180*e* at random on the monitor 180. As illustrated in FIG. 10, the subject images 180*c* to 180*e* of the present embodiment have striped visual targets DT1 (left inclination pattern), DT2 (non-inclination pattern), and DT3 (right inclination pattern), respectively, with a specified contrast set in the test-condition input process S100.

In the present embodiment, the contrast sensitivity test is conducted by requesting the subject to answer which of the striped visual targets DT1 to DT3 the striped visual target currently displayed on the monitor 180 is by using the controller 304. Specifically, when the subject judges that the striped visual target DT1 (left inclination pattern) is being presented, he/she operates a left button (not illustrated) of the controller 304. When the subject judges that the striped visual target DT2 (non-inclination pattern) is being presented, he/she operates an upper button (not illustrated) of the controller 304. When the subject judges that the striped visual target DT3 (right inclination pattern) is being presented, he/she operates a right button (not illustrated) of the controller 304. When the subject cannot recognize the direction of inclination of the presented striped visual target DT1, D2, or DT3, he/she operates a lower button (not illustrated) of the controller 304.

In step S309, the MPU 201 determines whether an input from the controller 304 is present (in other words, determines whether the subject has operated the controller 304). If no operation of the controller 304 is present, the process proceeds to step S311 (step S309: NO), and if an operation of the controller 304 is present, the process proceeds to step S313 (step S309: YES).

In step S311, the MPU 201 determines whether ten seconds have passed since a subject image 180*c*, 180*d*, or 180*e* was presented (since step S307). If ten seconds have not passed, the process returns to step S309 (step S311: NO), and if ten seconds have passed, the MPU 201 judges that the subject cannot recognize the striped visual target currently displayed on the monitor 180, and then the process proceeds to step S317 (step S311: YES) to present a next striped visual target (to proceeds to the next test).

In step S313, the MPU 201 analyzes an input to the controller 304 operated in step S309. Then, in the case of an input of the left button of the controller 304, the MPU 201 determines that the subject judged that the striped visual target DT1 (left inclination pattern) was being shown. In the case of an input of the upper button of the controller 304, the MPU 201 determines that the subject judged that the striped visual target DT2 (non-inclination pattern) was being shown. In the case of an input of the right button of the controller 304, the MPU 201 determines that the subject judged that the striped visual target DT3 (right inclination pattern) was being shown. Next, the process proceeds to step S315.

In step S315, the MPU 201 calculates the response time after the subject image 180*c*, 180*d*, or 180*e* was displayed (from step S307) until the subject operates the controller 304. Next, the process proceeds to step S317.

In step S317, the MPU 201 adds 1 to variable n for counting the number of tests and determines whether variable n is 6 (step S319). If variable n is not 6, steps S305 to S319 are repeatedly executed. If variable n is 6, the MPU 201 displays an operator image 301*c* on the external display 301 (step S321) and ends the central-visual-angle response speed test S300.

As described above, in the present embodiment, when variable n is one of 1 to 5 (in other words, five times), one of the subject images 180*c* to 180*e* is presented to the subject to conduct a contrast sensitivity test.

Note that in step S305, the operator image 301*b* displayed on the external display 301 is updated as appropriate while variable n is one of 1 to 5, and a progress display area PE for displaying the progress of the contrast sensitivity test shows the display state of the subject images 180*c* to 180*e* displayed on the monitor 180 (FIG. 11(*a*)). A pupil-diameter display area PD displays the diameters of the right and left pupils being continuously measured in a graph.

After the central-visual-angle response speed test S300 is finished, a test-result display area MR of the operator image 301*c* shows the striped visual targets presented in step S307, the inputs to the controller 304 analyzed in step S313, the test results (correct/incorrect results), the correct answer rate, the response times calculated in step S315, and the like (FIG. 11(*b*)).

In the present embodiment, the operator image 301*c* has a "switch display" button SB, which is configured to display the operator image 301*d* when clicked with the mouse 303 (FIG. 11(*c*)). The operator image 301*d* shows the subject's right and left eyeball images enlarged, and the eyeball-image display areas EBL and EBR each show a pair of scales SC1 and SC2 linearly extending horizontally and vertically movable. When the operator operates the mouse 303 and adjusts the positions of the scales SC1 and SC2 at the positions of the eyelids of each of the right and left eyeball images, palpebral-aperture display areas DL and DR of the operator image 301*d* show the subject's palpebral apertures.

As described above, when the central-visual-angle response speed test S300 is executed, not only whether the answer to the recognition of each striped visual target was correct or incorrect but also each response time is determined. Note that the determined response time can be used as an indicator for the degree of uncertainty in the recognition of each striped visual target. The information on the pupil diameters displayed in the pupil-diameter display area PD of the operator images 301*b* and 301*c* and the information on the palpebral apertures displayed in the palpebral-aperture display areas DL and DR of the operator image 301*d* can be used as indicators for judging whether the subject feels dazzled (in other words, whether the subject is having a stress).

[Peripheral-Visual-Angle Response Speed Test S400]

Figure 12:
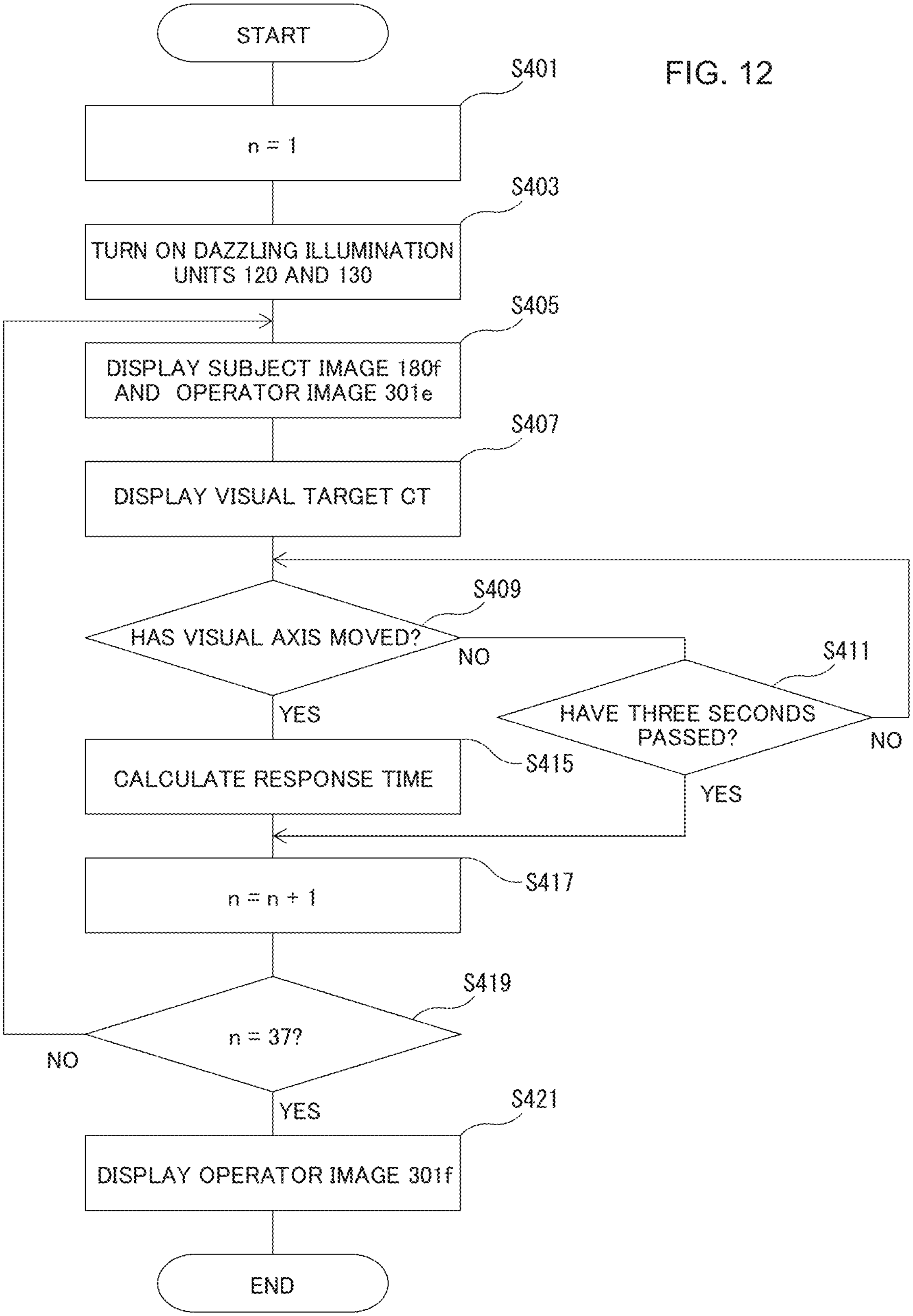
FIG. 12 is a flowchart of a peripheral-visual-angle response speed test executed by the contrast-sensitivity test device according to the first embodiment of the present invention.
Figure 13:
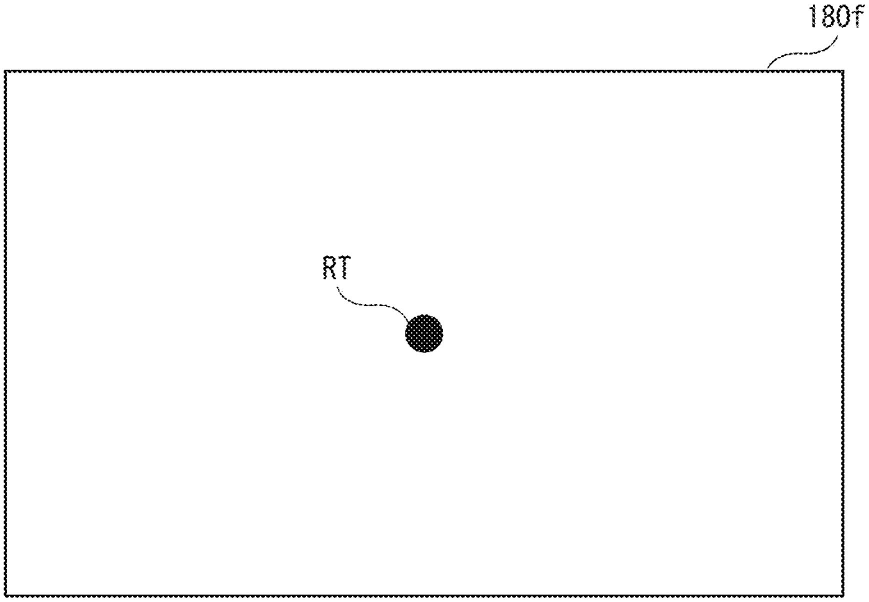
FIG. 13 shows subject images displayed in the peripheral-visual-angle response speed test in FIG. 12.
Figure 13:
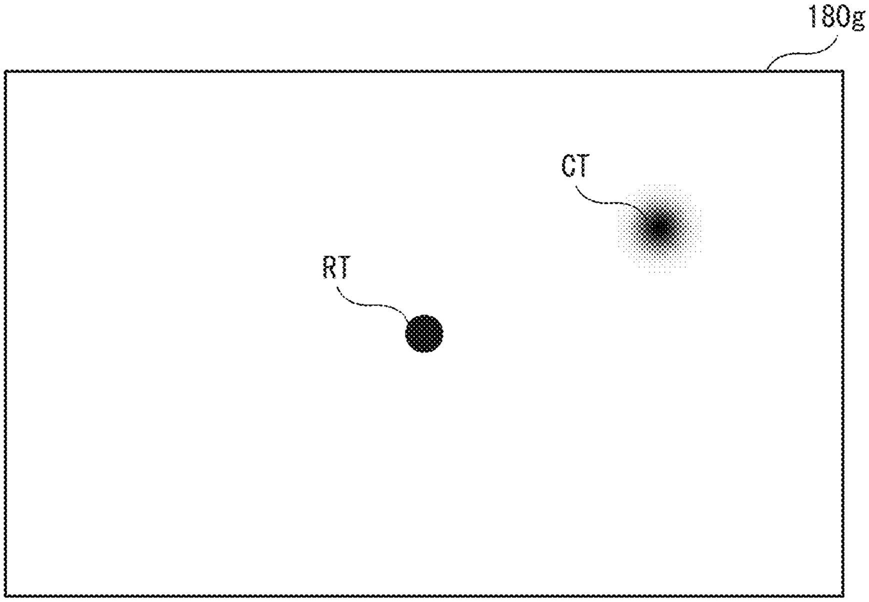
Figure 14:
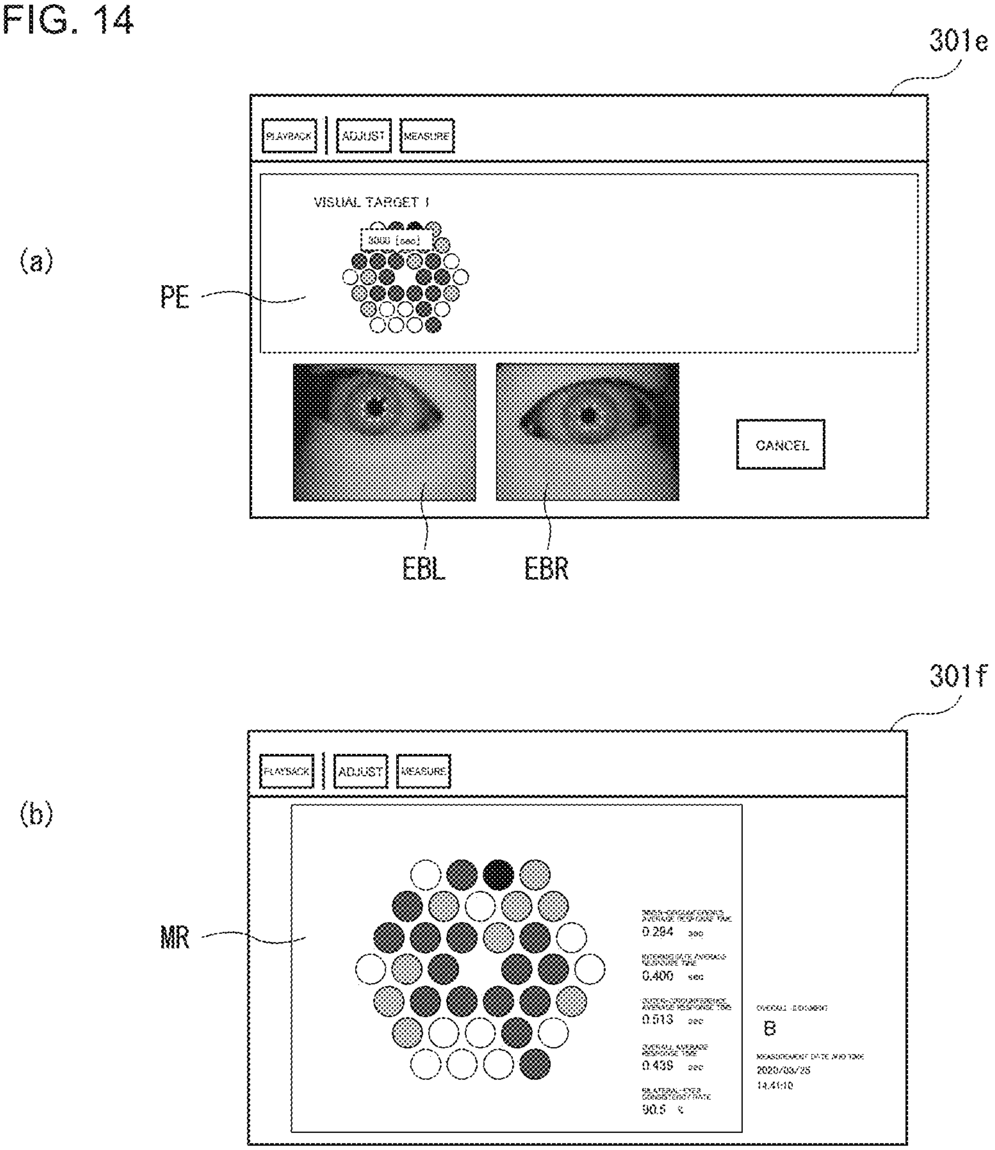
FIG. 14 shows operator images displayed in the peripheral-visual-angle response speed test in FIG. 12.

The peripheral-visual-angle response speed test S400 is a contrast sensitivity test in which visual targets having different contrasts are presented at positions away from the center, and the time until the subject gazes into each visual target is measured. FIG. 12 is a flowchart of the peripheral-visual-angle response speed test S400 executed by the MPU 201. FIG. 13 shows subject images 180*f* and 180*g* displayed on the monitor 180 and presented to the subject in the peripheral-visual-angle response speed test S400, and FIG. 14 shows operator images 301*e* and 301*f* displayed on the external display 301 and presented to the operator in the peripheral-visual-angle response speed test S400.

When the peripheral-visual-angle response speed test S400 is executed, the MPU 201 sets variable n for counting the number of tests to 1 (step S401) and turns on the dazzling illumination units 120 and 130 at a specified illuminance (in other words, turns on the LED chips 132 at a specified intensity) (step S403).

Next, the MPU 201 displays the subject image 180*f* on the monitor 180 and displays the operator image 301*e* on the external display 301. The MPU 201 also turns on the LEDs 111 to 118 of the IR illumination unit 110 and displays the right and left eyeball images from the eyeball cameras 150 and 160 in the eyeball-image display areas EBL and EBR in the operator image 301*e* (step S405).

As illustrated in FIG. 13, the subject image 180*f* of the present embodiment includes a circular reference visual target RT presented at approximately at the center of the field of view of the subject and a plurality of circular visual targets CT having different contrasts and presented with the reference visual target RT centered and at different positions around the reference visual target RT.

Figure 15:
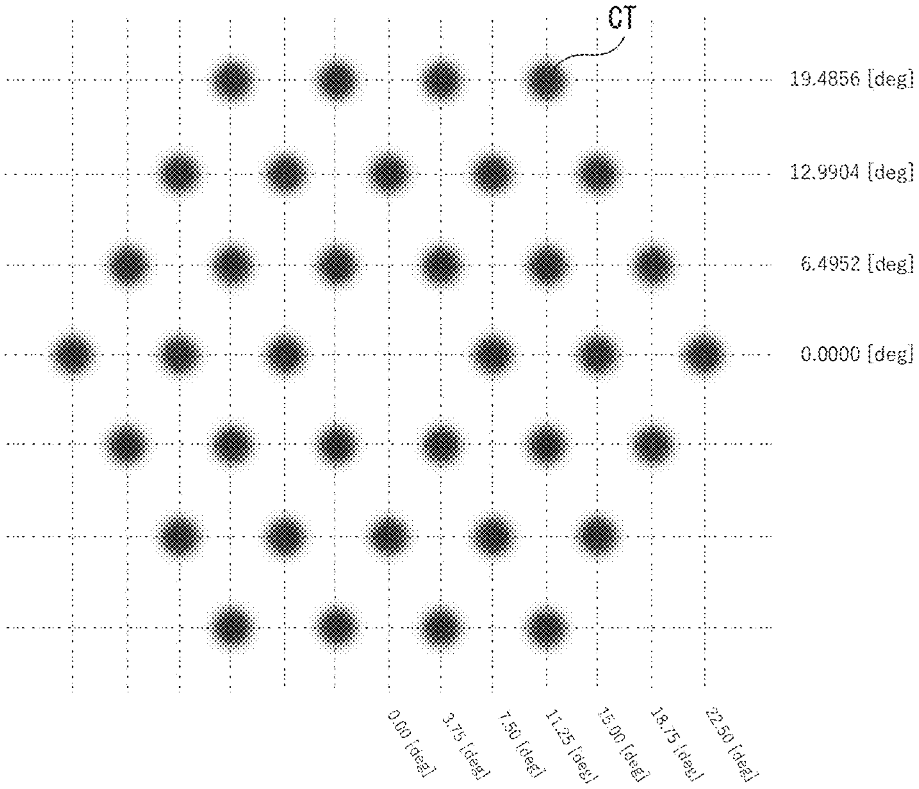
FIG. 15 shows the presentation positions of visual targets CT displayed in the peripheral-visual-angle response speed test in FIG. 12 and a diagram for explaining brightness.
Figure 15:
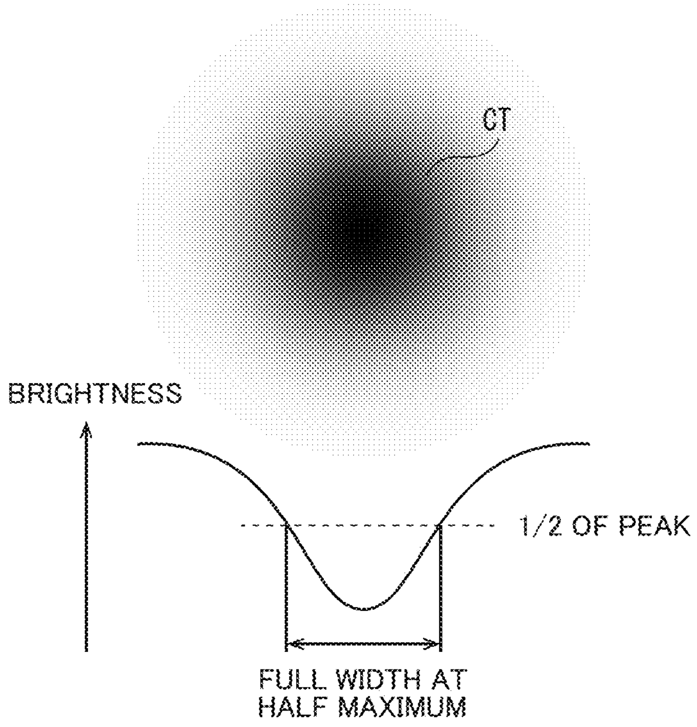

FIG. 15 shows diagrams for explaining the presentation positions (FIG. 15(*a*)) and the brightness (FIG. 15(*b*)) of the visual targets CT in the present embodiment. Note that in FIG. 15(*a*), the vertical axis represents the vertical visual angle, and the horizontal axis represents the horizontal visual angle. As illustrated in FIG. 15(*a*), the visual target CT of the present embodiment is randomly displayed with the reference visual target RT centered at the positions corresponding to visual angles of ±6.4952°, ±12.9904°, and ±19.486° in the vertical direction and ±3.75°, ±7.50°, ±11.25°, ±15.00°, ±18.75°, and ±22.50° in the horizontal direction.

As illustrated in FIG. 15(*b*), the visual target CT of the present embodiment is an approximately circular black image in which the brightness (luminance) varies according to a two-dimensional Gaussian function. The size of the visual target CT is set such that the full width at half maximum of the Gaussian function is equal to a visual angle of 0.775°. Note that the contrast of the visual target CT is expressed by the following equation:

$$\text{contrast}=(\text{maximum luminance}-\text{minimum luminance})/(\text{maximum luminance}+\text{minimum luminance})$$

where minimum luminance (cd/m$^2$) is the luminance at the center of the visual target CT, and the maximum luminance (cd/m$^2$) is the luminance of the background color of the visual target CT.

In step S407, the MPU 201 presents a visual target CT with a specified contrast at a position corresponding to one of the positions presented in FIG. 15(*a*) (FIG. 13(*b*)).

In the present embodiment, the contrast sensitivity test is conducted by requesting the subject to, when a visual target CT is presented, move his/her line of sight from the reference visual target RT to the visual target CT (in other words, requested to gaze into the visual target CT). Specifically, when the subject's visual axis (line of sight) moves from the reference visual target RT to the visual target CT, the movement is detected by the visual-axis detection process executed in step S207 in the calibration process S200, and the response time is thus measured.

In step S409, the MPU 201 determines by the visual-axis detection process whether the visual axis has moved (in other words, determines whether the subject has moved his/her line of sight to the visual target CT). If the visual axis has not moved, the process proceeds to step S411 (step 409: NO), and if the visual axis has moved, the process proceeds to step S413 (step S409: YES).

Note that in the present embodiment, the visual axis is determined to have moved when the visual axis has moved ⅗ of the straight-line distance between the reference visual target RT and the visual target CT.

In step S411, the MPU 201 determines whether three seconds have passed since the visual target CT was presented (since step S407). If three seconds have not passed, the process returns to step S409 (step S411: NO), and if three seconds have passed, the MPU 201 judges that the subject cannot recognize the visual target CT currently displayed on the monitor 180, and then the process proceeds to step S417 (step S411: YES) to present a next visual target CT (to proceed to the next test).

In step S415, the MPU 201 calculates the response time after presenting the visual target CT (from step S407) until detecting the movement of the visual axis in step S409. Next, the process proceeds to step S417.

In step S417, the MPU 201 adds 1 to variable n for counting the number of tests and determines whether variable n is 37 (step S419). If variable n is not 37, the process repeatedly executes steps S405 to S419, and if variable n is 37, the MPU 201 displays the operator image 301*f* on the external display 301 (step S421), and ends the peripheral-visual-angle response speed test S400.

As described above, in the present embodiment, when variable n is one of 1 to 36 (in other words, 36 times), a visual target CT is presented randomly at one of the presentation positions illustrated in FIG. 15(*a*), and the contrast sensitivity test is conducted.

Note that in step S405, the operator image 301*e* displayed on the external display 301 is updated as appropriate while variable n is one of 1 to 36, and the display state of the visual target CT on the monitor 180 is displayed in the progress display area PE for displaying the progress of the contrast sensitivity test (FIG. 14(*a*)).

When the peripheral-visual-angle response speed test S400 is finished, the test-result display area MR of the operator image 301*f* shows the relationship between the position of the visual target CT presented in step S407 and the response time calculated in step S415 in a mapping diagram, and the judgment result is displayed in ranking according to the relationship between the contrast of the visual target CT and the response time (FIG. 14(*b*)). The position of each circular mark in the test-result display area MR of the operator image 301*f* corresponds to the position of each visual target CT, and the color (the shade of gray in FIG. 14(*b*)) expresses the response time calculated in step S415. Note that in the present embodiment, a darker gray color indicates a higher reaction speed, while a lighter gray color indicates a slower reaction speed. In the test-result display area MR, "inner-circumference average response time" indicates the average response time of the 6 visual targets CT near the center (located on the inner circumference), "outer-circumference average response time" indicates the average response time of the outermost 18 visual targets CT (located on the outer circumference), "intermediate average response time" indicates the average response time of the 12 visual targets CT located in the middle (located between the inner circumference and the outer circumference), "overall average response time" indicates the average response time of all of the (36) visual targets CT, and "bilateral-eyes consistency rate" indicates the rate of consistency between the lines of sight of the right and left eyes at the moment when the subject looks at each visual target CT (in other words, an indicator showing whether the subject was looking with both eyes). "overall judgment" shows the rank determined according to the overall average response time. In the present embodiment, the overall judgment is determined in five ranks: S, A, B, C, and D, in descending order of the reaction speed.

As described above, when the peripheral-visual-angle response speed test S400 is executed, the response time for each visual target CT is calculated and displayed in association with the presentation position of each visual target CT. In addition, the judgment result is displayed in ranking according to the relationship between the contrast of each visual target CT and the response time (in other words, the result of the contrast sensitivity test). In other words, the contrast sensitivity test is conducted automatically and objectively.

The present embodiment has been described above, but the present invention is not limited to the configuration described above. Various modifications can be made within the scope of the technical ideas of the present invention.

For example, although the dazzling illumination units 120 and 130 are turned on at a specified illuminance (in other words, the LED chips 132 are turned on at a specified intensity) in the central-visual-angle response speed test S300 and the peripheral-visual-angle response speed test S400 in the present embodiment, the present invention not necessarily limited to the configuration above. The central-visual-angle response speed test S300 and the peripheral-visual-angle response speed test S400 may be executed with the dazzling illumination units 120 and 130 turned off, with the dazzling illumination units 120 and 130 flashing at a specified period, or with the dazzling illumination units 120 and 130 changed.

Although the description of the present embodiment is based on the assumption that the central-visual-angle response speed test S300 and the peripheral-visual-angle response speed test S400 are executed sequentially, one of the central-visual-angle response speed test S300 and the peripheral-visual-angle response speed test S400 may be executed as necessary as a possible configuration.

Although the description of the present embodiment is based on the assumption that visual targets CT having specified contrasts are used in the central-visual-angle response speed test S300, the color, brightness, contrast, and background color of the visual targets CT may be changed as appropriate depending on details of the test.

Although the description of the present embodiment is based on the assumption that the visual targets CT are presented at 36 presentation positions in the peripheral-visual-angle response speed test S400, the present invention is not necessarily limited to the configuration described above. For example, only the 6 presentation positions close to the center may be used as a possible configuration.

Although the description of the present embodiment is based on the configuration in which various visual targets that the subject views are presented on the monitor 180 located in the test unit 100, the present invention is not limited to the configuration described above. A screen may be provided instead of the monitor 180, and the various visual targets that the subject views may be presented on the screen. Alternatively, a plurality of screens (for example, sheets of paper) on each of which a different one of the visual targets is displayed are provided, and the screens may be switched and sequentially placed within the subject's field of view.

Second Embodiment

[Configuration of Optical-Element Evaluation Device]

Figure 16:
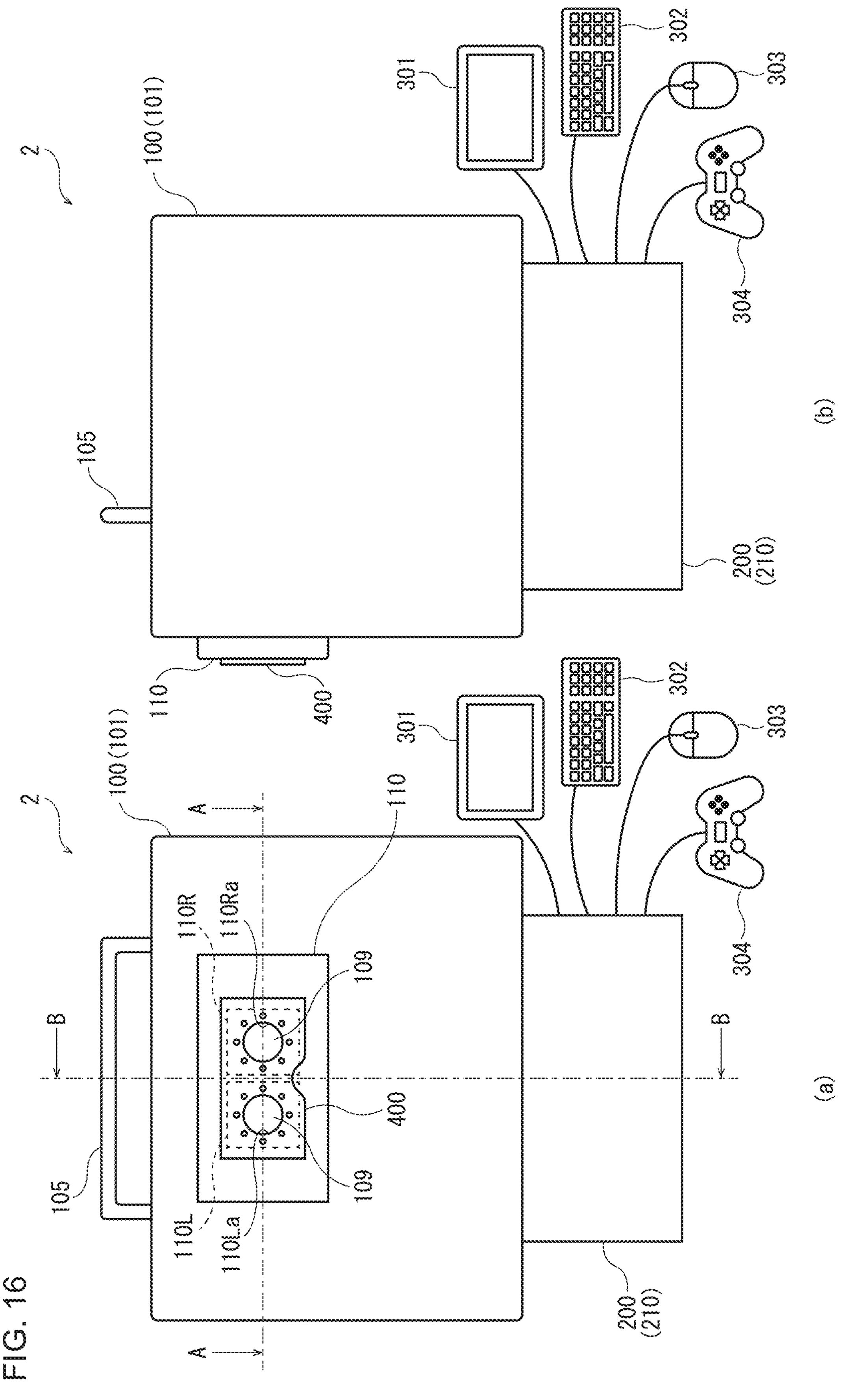
FIG. 16 shows diagrams illustrating the configuration of an optical-element evaluation device according to a second embodiment of the present invention.

FIG. 16 shows diagrams illustrating the configuration of an optical-element evaluation device 2 according to a second embodiment of the present invention. The optical-element evaluation device 2 of the present embodiment is assumed to be placed in a shop such as an eyeglass shop and used for a user having an intention to buy eyeglasses or sunglasses to evaluate the lenses of eyeglasses or sunglasses in advance (before purchase). The optical-element evaluation device 2 is different from the contrast-sensitivity test device 1 of the first embodiment in that it has an evaluation-lens holder 400 on the front face (the face on the subject side) of the IR illumination unit 110 as illustrated in FIG. 16.

Figure 17:
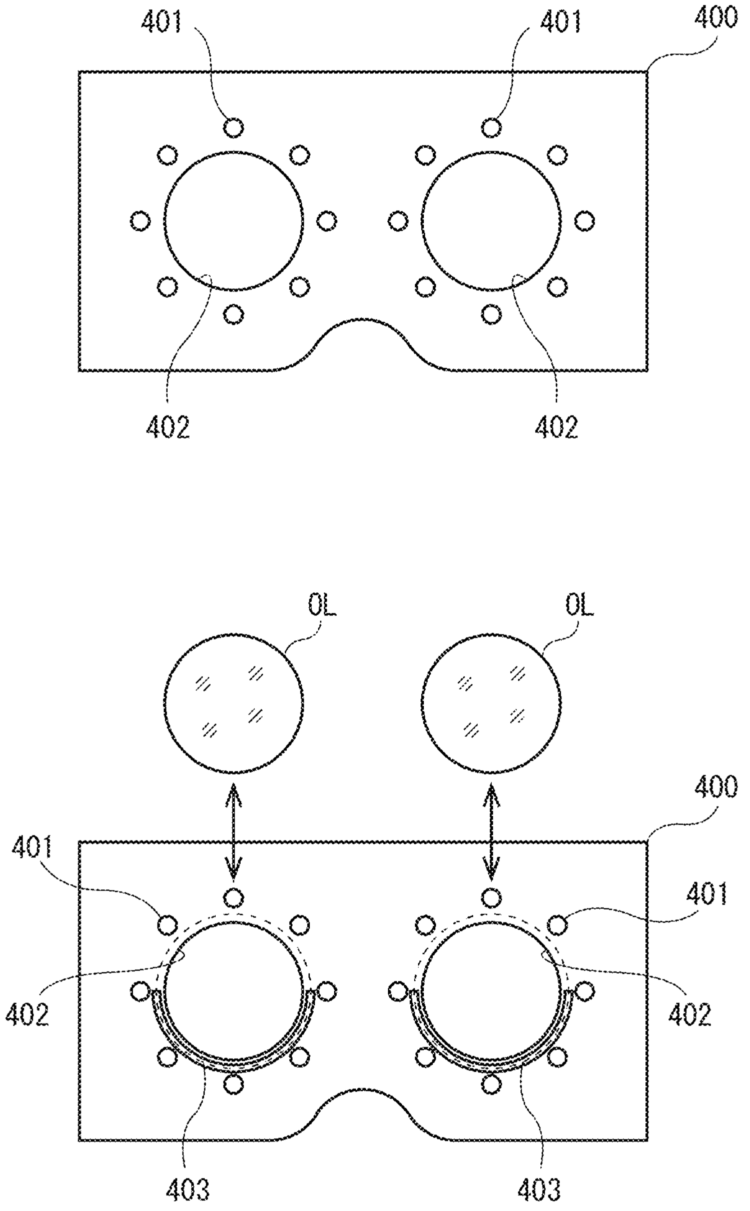
FIG. 17 shows diagrams illustrating the configuration of an evaluation-lens holder of the optical-element evaluation device according to the second embodiment of the present invention.

FIG. 17 shows diagrams for explaining the configuration of the evaluation-lens holder 400. FIG. 17(*a*) is its front view, and FIG. 17(*b*) is its back view.

The evaluation-lens holder 400 is an approximately rectangular member made of a cloth or a resin and configured to support the lenses OL for evaluation between the subject's eyeballs and the test unit 100.

As illustrated in FIG. 17, the evaluation-lens holder 400 has two circular openings 402 extending through from the front face to the back face of the evaluation-lens holder 400 and 16 through holes 401 located so as to circularly surround the openings 402. The back face of the evaluation-lens holder 400 has lens supports 403 provided along the lower portions of the openings 402, so that right and left lenses OL for evaluation can be placed into and removed from (inserted into and pulled out from) the lens supports 403. Note that right and left lenses OL may have the same characteristics (such as prescription strength, color, and transmittance), or right and left lenses OL may have different characteristics according to the characteristics of each eye (such as wavelength sensitivity and brightness sensitivity).

The openings 402 are for the user to look into the test unit 100. The through holes 401 are openings located at the positions corresponding to the LEDs 111 to 118 of the IR illumination unit 110 and configured such that the LEDs 111 to 118 are exposed through the through holes 401, and infrared light IR from the LEDs 111 to 118 is not blocked, in the state in which the evaluation-lens holder 400 is attached to the IR illumination unit 110.

Note that the evaluation-lens holder 400 of the present embodiment is configured to be fixed to the front face of the IR illumination unit 110 with a magnet (not illustrated).

As described above, the optical-element evaluation device 2 of the present embodiment is configured such that the lenses of eyeglasses or sunglasses desired by the user can be easily attached to or detached from the test unit 100.

Thus, the user can take a contrast sensitivity test easily with his/her desired lenses. Specifically, since the optical-element evaluation device 2 is capable of reproducing an illumination environment of several conditions by replacing the color-temperature adjustment filters 138 and 139 of the dazzling illumination units 120 and 130 as described above, the user can experience (evaluate) the effects of wearing eyeglasses or sunglasses depending on their usage environment.

Since the color, brightness, contrast, background color of the visual targets CT can be changed as appropriate in the central-visual-angle response speed test S300 as described above, an evaluation depending on the characteristics of lenses can be conducted by changing the evaluation environment as appropriate, for example, setting the background color to the most difficult color to see and setting the color of the visual targets to the color having the highest contrast to the background color depending on the characteristics of lenses for evaluation (such as transmittance characteristics and color).

In addition, since the peripheral-visual-angle response speed test S400 shows how the subject can see through lenses, objectively in ranking as described above, a user having an intention to buy lenses can judge objectively whether lenses are suitable for the user by the evaluation.

In addition, since the optical-element evaluation device 2 provides information on the pupil diameters and the palpebral apertures during the contrast sensitivity test as an indicator for judging whether the user feels dazzled (in other words, whether the user is having a stress) as described above, it is possible to judge from such information objectively whether lenses are suitable for the user by evaluation.

Although the description of the present embodiment is based on the assumption that the optical-element evaluation device 2 is used for evaluating the lenses of eyeglasses or sunglasses, objects of evaluation may be any optical elements or optical materials that are placed immediately in front of the user's eyes. Examples include contact lenses, goggles (for all sports such as swimming, skiing, and riding), helmet shields, windshields, and window glasses. Although the description of the optical-element evaluation device 2 is based on the assumption that it is used to evaluate the lenses of eyeglasses or sunglasses in advance (before purchase), the optical-element evaluation device 2 is not necessarily limited to such usage. Products that are already owned by the user may be evaluated.

Note that it should be understood that the embodiments disclosed herein are examples in all aspects and are not restrictive. The scope of the present invention is defined not by the above description but by the claims and is intended to include all modifications within the scope of the claims and the equivalents thereof.

REFERENCE SIGNS LIST

1 contrast-sensitivity test device
2 optical-element evaluation device
100 test unit
101 upper casing
101*a* opening
105 filter replacement handle
110 IR illumination unit
110L left-eye unit
110La opening
110R right-eye unit
110Ra opening
111 LED
112 LED
113 LED
114 LED
115 LED
116 LED
117 LED
118 LED
119 cover glass
120 dazzling illumination unit
130 dazzling illumination unit
131 substrate
132 LED chip
133 case
133*a* opening
134 diffusion plate
135 heat sink
135*a* heat dissipation fin
138 color-temperature adjustment filter
139 color-temperature adjustment filter
140 hot mirror
150 eyeball camera
160 eyeball camera
170 reflection mirror
172 reflection surface
180 monitor
180*a* subject image
180*b* subject image
180*c* subject image
180*d* subject image
180*e* subject image
180*f* subject image
180*g* subject image
182 display surface
200 control unit
201 MPU
202 ROM
203 RAM
204 hard disk
210 lower casing
301 external display
301*a* operator image
301*b* operator image
301*c* operator image
301*d* operator image
301*e* operator image
301*f* operator image
302 keyboard
303 mouse
304 controller
400 evaluation-lens holder
401 through hole
402 opening
403 lens support
CCL circle
CS CAL execution switch
CT visual target
DL palpebral-aperture display area
DR palpebral-aperture display area
DT1 striped visual target
DT2 striped visual target
DT3 striped visual target
EBL eyeball-image display area
EBR eyeball-image display area
GT gaze visual target
IR infrared light
L display light
MKL reference marker
MKR reference marker
MR test-result display area
OL lens
P illumination light
PD pupil-diameter display area
PE progress display area
RT reference visual target
SB button
SC1 scale
SC2 scale
n variable

The invention claimed is:

1. A contrast-sensitivity test device comprising:

an illumination unit that emits illumination light such that a field of view of a subject is in a specified illumination environment;

a visual target presentation unit that is located within the field of view of the subject and that switches and sequentially presents a plurality of visual targets having different contrasts;

a response-time measurement unit that, when the illumination light is emitted, measures a response time after each visual target is presented until the subject recognizes the visual target; and a casing that houses the illumination unit, the visual target presentation unit, and the response-time measurement unit, wherein the visual target presentation unit presents a reference visual target approximately at a center portion of the field of view of the subject and presents each visual target at a position different from the position of the reference visual target for a specified time, the positions at which the plurality of visual targets presented are different from one another, and the response-time measurement unit detects a first line of sight when the subject visually recognizes the reference visual target and a second line of sight when the subject visually recognizes each visual target;

determines a line-of-sight vector from the first line of sight and the second line of sight; and measures the response time from the line-of-sight vector.

2. The contrast-sensitivity test device according to claim 1, wherein the response-time measurement unit includes three or more IR illumination devices each of which emits testing light toward an eyeball of the subject, an image capturing device that captures a reflected image formed by the testing light reflected on the eyeball, and a line-of-sight vector calculation unit that calculates the line-of-sight vector from the reflected image.

3. The contrast-sensitivity test device according to claim 2, wherein the image capturing device captures an image of an eyeball of the subject and the periphery of the eyeball, and the contrast-sensitivity test device further comprises an image processing unit that calculates at least one of the palpebral fissure width and the pupil diameter of the subject from data of the image captured by the image capturing device.

4. The contrast-sensitivity test device according to claim 1, wherein the response-time measurement unit includes an input unit that receives an input from the subject, and the response-time measurement unit measures the time after each visual target is presented until the input unit receives an input, as the response time.

5. The contrast-sensitivity test device according to claim 1, wherein the illumination unit emits the illumination light toward an eyeball of the subject such that the subject feels dazzled.

6. The contrast-sensitivity test device according to claim 1, wherein the illumination unit is configured such that the color temperature of the illumination light is changeable.

7. A contrast-sensitivity test device comprising:

an illumination unit that emits illumination light such that a field of view of a subject is in a specified illumination environment;

a visual target presentation unit that is located within the field of view of the subject and that switches and sequentially presents a plurality of visual targets having different contrasts;

a response-time measurement unit that, when the illumination light is emitted, measures a response time after each visual target is presented until the subject recognizes the visual target; and a casing that houses the illumination unit, the visual target presentation unit, and the response-time measurement unit, wherein the illumination unit includes a plurality of LED elements that emit light similar to natural light, a diffusion plate that diffuses the light emitted from the plurality of LED elements, and a color-temperature conversion filter that converts the light having passed through the diffusion plate, into the illumination light having a specified color temperature, and the color-temperature conversion filter is replaceable.

8. The contrast-sensitivity test device according to claim 1, wherein the visual target presentation unit includes an image display device that displays an image of each visual target.

9. The contrast-sensitivity test device according to claim 1, wherein the visual target presentation unit includes a screen and a projection device that projects and displays each visual target on the screen.

10. The contrast-sensitivity test device according to claim 1, wherein the visual target presentation unit includes a plurality of screens on each of which a different one of the visual targets is displayed, and the screens are switched and sequentially placed within the field of view of the subject.

11. The contrast-sensitivity test device according to claim 1, wherein each visual target has an approximately circular shape in which brightness varies according to a two-dimensional Gaussian function.

12. The contrast-sensitivity test device according to claim 1, wherein the visual targets include a striped pattern in which a white line and a black line are repeated alternately.

13. An optical-element evaluation device comprising:

the contrast-sensitivity test device according to claim 1; and an optical element that is placed in front of an eyeball of the subject so as to be replaceable.

14. A contrast-sensitivity test method comprising:

emitting illumination light such that a field of view of a subject is in a specified illumination environment;

switching and sequentially presenting a plurality of visual targets having different contrasts in the field of view of the subject; and measuring, when the illumination light is emitted, a response time after each visual target is presented until the subject recognizes the visual target, wherein presenting the plurality of visual targets in the field of view of the subject presents a reference visual target approximately at a center portion of the field of view of the subject and presents each visual target at a position different from the position of the reference visual target for a specified time, the positions at which the plurality of visual targets presented are different from one another, and the measuring each response time includes detecting a first line of sight when the subject visually recognizes the reference visual target and a second line of sight when the subject visually recognizes each visual target;

determining a line-of-sight vector from the first line of sight and the second line of sight; and measuring the response time from the line-of-sight vector.

15. The contrast-sensitivity test method according to claim 14, wherein the measuring each response time includes emitting testing light toward an eyeball of the subject, capturing a reflected image formed by the testing light reflected on the eyeball, and calculating the line-of-sight vector from the reflected image.

16. The contrast-sensitivity test method according to claim 14, wherein the measuring each response time includes receiving an input from the subject, and measuring the time after each visual target is presented until the input is received, as the response time.

17. The contrast-sensitivity test method according to claim 14, wherein the illumination light is emitted toward an eyeball of the subject such that the subject feels dazzled.

18. The contrast-sensitivity test method according to claim 14, wherein the color temperature of the illumination light is changeable.

19. The contrast-sensitivity test method according to claim 14, further comprising capturing an image of an eyeball of the subject and the periphery of the eyeball and calculating at least one of the palpebral fissure width and the pupil diameter of the subject from data of the captured image.

20. An optical-element evaluation method comprising the contrast-sensitivity test method according to claim 14, further comprising placing an optical element in front of an eyeball of the subject.

* * * * *